United States Patent [19]

Raychaudhuri

[11] Patent Number: 5,270,202

[45] Date of Patent: Dec. 14, 1993

[54] ANTI-IDIOTYPIC ANTIBODIES TO HUMAN MELANOMA-ASSOCIATED PROTEOGLYCAN ANTIGEN

[76] Inventor: Syamal Raychaudhuri, 3716 Carmel View Rd., San Diego, Calif. 92130

[21] Appl. No.: 680,808

[22] Filed: Mar. 12, 1991

Related U.S. Application Data

[63] Continuation-in-part of Ser. No. 431,426, Nov. 3, 1989, abandoned.

[51] Int. Cl.$^5$ .................. C07K 15/28; C07K 15/00; C12P 21/08; C12N 5/18
[52] U.S. Cl. .................... 435/240.27; 530/387.2; 530/387.3; 530/388.85; 530/389.7; 530/388.8
[58] Field of Search ............ 530/387.3, 387.2, 388.85, 530/389.7, 388.8; 435/240.27

[56] References Cited

U.S. PATENT DOCUMENTS 4,918,164  4/1990  Hellstrom et al. ............... 530/387.3

OTHER PUBLICATIONS

Kusama et al. Cancer Research 47:4312 (1987).
Kantor et al. Cancer Research 46:5223 (1986).
Wilson et al. Int. J. Cancer 28:293 (1981).
DeFrietag et al. May 15, 1985 EP 0141783.
Lazar et al. Molec. Cellul. Biol. 8: 1247 (1988).
Waldmann Science 252: 1657 (1991).
Burgess et al. J. Cell. Biol. 111: 2129 (1990).
Tao et al. Journal of Immunology vol. 143 1989 p. 25, 95.

*Primary Examiner*—Y. Christina Chan
*Assistant Examiner*—Lila Feisee
*Attorney, Agent, or Firm*—Kenneth J. Woolcott; Richard P. Burgoon, Jr.

[57] ABSTRACT

This application discloses a novel anti-idiotypic antibody, IMelpg2 and equivalents thereof, as well as, antibody fragments, peptides or antisera capable of reacting with at least one of the idiotopes of: (a) murine monoclonal antibody MEM136 and derivatives thereof; (b) a monoclonal antibody secreted by hybridomas from any species having the same immunological specificity as antibody MEM136; or (c) any polyclonal antibodies from any species having the same immunological specificity as antibody MEM136, wherein (a), (b), or (c) is capable of reacting with a specific determinant (epitope) of a MPG antigen are described, together with their preparation and use in the diagnosis, monitoring and treatment of tumors such as melanoma or other diseased cells that express the MPG epitope recognized by antibody MEM136.

2 Claims, 19 Drawing Sheets

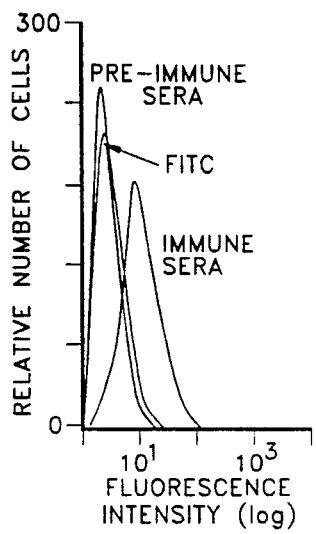
FIG. 15A
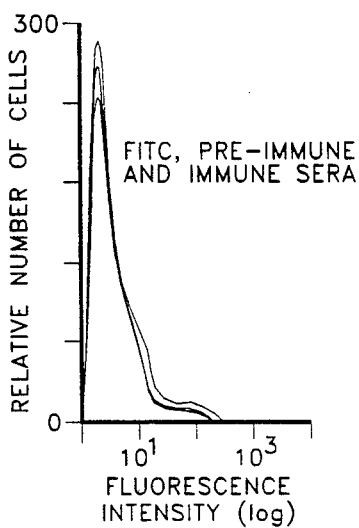
FIG. 15C
FIG. 15B
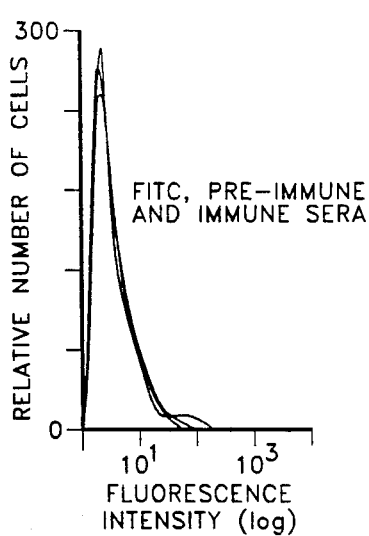
FIG. 15D
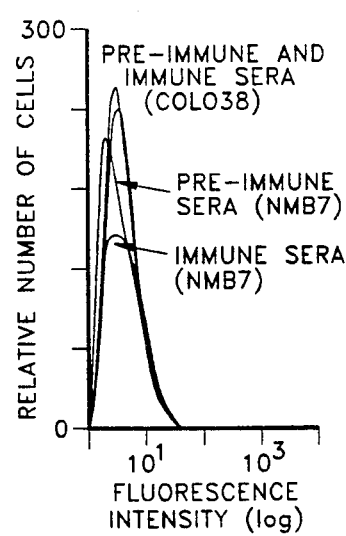
FIG. 15E

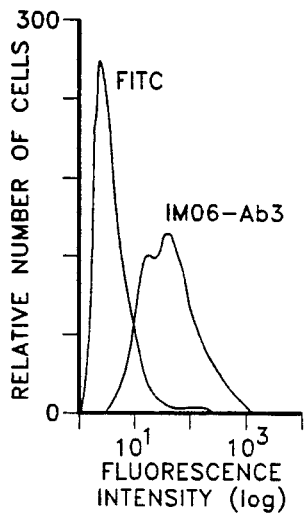
FIG. 17A
FIG. 17B
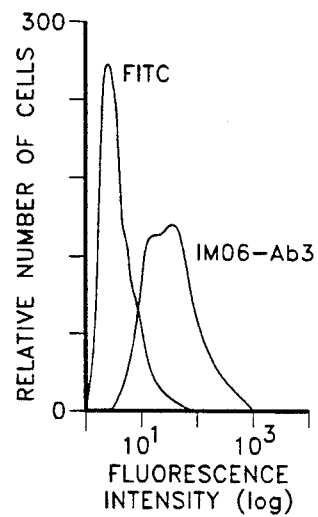
FIG. 17C
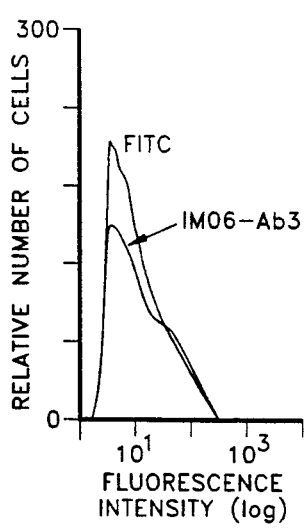
FIG. 17D
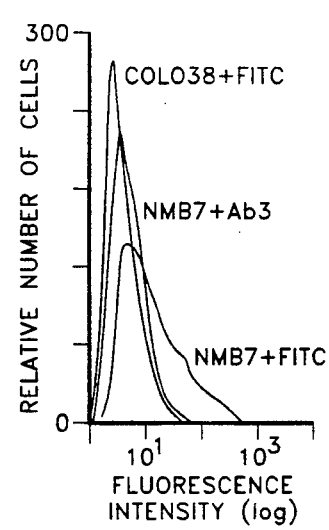
FIG. 17E

ANTI-IDIOTYPIC ANTIBODIES TO HUMAN MELANOMA-ASSOCIATED PROTEOGLYCAN ANTIGEN

REFERENCE TO RELATED APPLICATION

This application is a continuation-in-part of U.S. Ser. No. 07/431,426, filed Nov. 3, 1989, now abandoned.

FIELD OF THE INVENTION

The present invention relates generally to the development of antibodies that are specifically designed to enhance immunological activity by the host against a tumor. More particularly, the present invention relates to antibody reagents that are directed to antigens expressed on the melanoma cells and are useful in the treatment of patients suffering from melanoma. Such antigens include, the High Molecular Weight-Melanoma Associated Antigen ("HMW-MAA"), also know as the human melanoma-associated proteoglycan ("MPG"). MEM136 is a monoclonal antibody that recognizes an epitope of undefined structure on the MPG antigen.

Accordingly, this invention is in the field of anti-idiotypic antibodies to the anti-MPG antibody MEM136 and its immunological equivalents. The anti-idiotype antibody IMelpg2 (also known as "IM32") to antibody MEM136 has been discovered and evaluated in animal model systems.

This invention also is in the field of diagnosis, monitoring and treatment of tumors, such as melanoma or other diseased cells that express the MPG epitope recognized by antibody MEM136, by the administration and application of such anti-idiotypic antibodies.

BACKGROUND OF THE INVENTION

Introduction

Antigens are substances that can induce an immune response, for example, a "humoral response" or B-cell lymphocyte response that results in antibody production. Another typical response is the stimulation of T-cells, viz., a "cellular response." (T-cells are another type of lymphocyte that have undergone differentiation in the thymus gland.) T-cells are capable of destroying abnormal cells such as those infected by certain types of viruses or other pathogens. T-cells also are involved in antibody production by B-cells. Accordingly, an antigen can react either with antibodies or with receptors on the T-cells that it stimulates. Antibodies and T-cell receptors are specific for the inducing antigen.

Antibodies and T-cell receptor molecules possess variable regions that are responsible for specific antigenic recognition. The region of the antigen that actually binds to the antibody or T-cell receptor is termed the antigenic determinant or "epitope." Similarly, the variable regions of antibodies and T-cell receptors also contain determinants, or "idiotypes" that are immunogenic and are capable of initiating an anti-antibody antibody response, i.e., an anti-idiotype ("anti-id") immune response.

More particularly, idiotopes are associated with the variable regions of antibody and T-cell receptors. These variable regions confer antibody and T-cell receptor specificity for antigens. Idiotypes are immune system markers on antibodies and T-cell receptors. An idiotype is immunologically defined by reactivity with more than one anti-idiotypic antibody that recognizes an idiotypic determinant or idiotope within a given idiotype; i.e., an idiotype is made up of a collection of idiotopes. Idiotopes are best defined by their binding to monoclonal anti-idiotypic antibodies. It also should be noted that idiotopes are distinct from isotypic (immunoglobulin class-specific), xenotypic (species specific) and allotypic (certain population sub-group specific) determinants.

Each antibody and T-cell receptor has at least one paratope that is the binding site for an antigen determinant (the epitope). A paratope may serve as an idiotope, i.e., the paratope may stimulate an anti-idiotypic response in which, like the original antigen, an anti-anti-idiotopic antibody bind to an epitope within the paratope. A subset of anti-paratope anti-idiotype ("anti-id") antibodies may mimic the immunologic properties of the original antigen and are known as "Ab2 betas" or "internal images" antibodies. In addition to the anti-paratopic anti-ids that mimic the original antigen, other anti-id antibodies define antibody and T-cell receptor idiotopes that also participate in the regulation of immune responses. These idiotypes are termed regulatory idiotypes and they are not necessarily "internal images" of the original antigen. For a general discussion of these background principles, see Burdette, S. and Schwartz, R., *New Eng. J. of Med.* 317:219 (1987).

The Idiotypic Network

In any given species or individual, the number of different antibodies and T-cell receptors is very large ($>10^7$). Each antibody and T-cell receptor expresses several idiotopes that are linked through a regulatory network to complementary anti-idiotopes. Jerne, N., *Ann. Immunol.* 1256:373 (1974), proposed that the immune system is regulated by an interactive network composed of idiotypes and anti-idiotypes. There is a large body of experimental evidence indicating that the function of the idiotypic network is to maintain the homeostasis of the immune system and to regulate immune responses. As idiotypes are expressed by B-cells and T-cells, the idiotypic network encompasses both humoral (antibody) and cellular (T-cell mediated) immune responses. Specific immune responses may be regulated by specific anti-idiotypic antibodies either on a one to one basis, or in groups through shared idiotopes. (See, Goldberg., et al., *J. Exp. Med.* 158:515 (1983)).

Anti-Idiotype Therapy

Recently, the use of "internal image" anti-idiotypes in therapy has been suggested and demonstrated in several experimental systems (EPO App. No. 848105169, filed Oct. 15, 1984, Pub. No. 0141783; Nisonoff, A., and Lamoyi E., *Clin. Immunol. Immunopatholo.* 21:397 (1981); Kennedy, et al., *Biotechniques* 3:4040 (1985)). These internal image anti-idiotypes have been used as surrogates for antigens in generating specific immune responses against viral, bacterial and parasitic infections and cancers (Herlyn, et al., *Science* 232:100 (1986); Raychaudhuri, et al., *J. Immunol.* 137:1743 (1986)).

Currently, internal image polyclonal and monoclonal anti-idiotype antibodies are being used for active immunotherapy in animals and man. The methods for generating such anti-idiotype antibodies are well known to those of skill in the art. Briefly, the process of generating such internal image anti-idiotypes is as follows: (1) an antibody is made against an antigen or an infectious agent (this antibody is called an "Ab1"); and, (2) anti-idiotypic antibodies ("Ab2s") are made against these Ab1s. These antimaids (Ab2s) are screened for the expression of idiotypes that mimic the immunological properties of the initial antigen (such as that expressed by a tumor or infectious agent). This screening consists of inhibiting the Ab1-Ab2 interaction by the original antigen and the biological testing of the anti-idiotypes (Ab2) as a surrogate antigen in vivo. This testing is done in animals and has been demonstrated previously for internal image anti-idiotypes representing tumor antigens and infectious agents (Kennedy, et al., *Biotechniques* 3:4040 (1985); Herlyn, et al., *Science* 232:100 (1986); Raychaudhuri, et al., *J. Immunol.* 137:1743 (1986).

Prior art efforts to generate useful active tumor immunotherapies, however, have met with unpredictable success. One may postulate several reasons for the limited success and unpredictable results seen in the prior art. First, many tumor antigens are difficult to isolate. Tumor antigens often are not present in significant concentration in tumor masses or on individual cultured tumor cells. Secondly, tumor antigens often are poorly immunogenic. The poor immunogenicity may be a result of the presence of other constituents of tumor cells that suppress immunologic reactivity, or because the antigens are not uniquely expressed by tumor cells. Generally, antigens that the immune system recognizes as "self" will not provoke a significant immune response. Thus, the use in tumor immunotherapy of anti-idiotype antibodies as tumor antigen surrogates has a number of advantages, including the ability to manufacture such antibodies in large quantities and the increased immunogenicity of such antibodies as compared to natural antigens.

Moreover, prior art efforts to generate useful internal image anti-idiotypes also have met with unpredictable success. With reference to the idiotypic network, many anti-idiotype antibodies, for reasons that are unclear, simply are unable to induce efficacious immune responses in vivo despite preliminary analyses indicating that they mimic the properties of the original antigen. Even anti-idiotype antibodies that demonstrate the proper specificity in vitro, or even partially in vivo, often are unable to stimulate the immune network to generate a therapeutically effective immune response. Presumably, these ineffective internal image Ab2s do not induce the appropriate regulatory circuits of the immune network of idiotype/anti-idiotype interactions to elicit effective immunity. In short, discovery of therapeutically useful anti-idiotype antibodies is as much art as science. Against this backdrop of unpredictability and uncertainty, the novel anti-idiotype antibodies herein described have been successfully tested to produce anti-melanoma tumor response in animals.

Melanoma Antigen Targets

One appropriate target to develop immunotherapeutic approaches to melanoma is the melanoma-associated chondroitin sulfate proteoglycan ("MPG") antigen, also referred to as the high molecular weight melanoma-associated antigen ("HMW-MAA"). Applicant's results show that attempts to induce cellular and humoral responses against MPG may result in intervention of tumor growth. The MPG consists of two non-covalently associated glycopolypeptides. One has an apparent molecular weight of 280Kd, and the other has an apparent molecular weight greater than 440Kd. MPG is synthesized and expressed by human melanoma cells (Spiro, et al., *J. Biol. Chem.* 264:1779 (1989); Esko, et al., *Science* 241:1092 (1988)). Proteoglycans are glycoproteins with glycosaminoglycan (GAG) polysaccharide chains covalently attached to the serine amino acid residue in their core. The MPG core protein is initially translated as a precursor with a molecular mass of 240Kd with asparagine-N-linked oligosaccharides of the high mannose type. Trimming and subsequent processing of the N-linked oligosaccharide to the "complex" form results in the conversion of the 240Kd component to a 250Kd form. The addition of chondroitin sulfate GAG side chains to the 250Kd core protein converts it to a high molecular weight 450Kd) proteoglycan form. Both 250Kd and >450Kd forms are expressed on the melanoma cell surface (Spiro, et al., *J. Biol. Chem.* 264:1779 (1989)). MPG plays a key role in determining the fate of tumor growth and metastasis (Herlyn, et al., *Ann. Rev. Immunol.* 6:283 (1988); Robertson, et al., *Cancer Res.* 49:1816 (1989)). Cell surface protein molecules are involved in interactions with adjacent cells and form complex footpads that make contact with substratum (Herlyn, et al., *Ann. Rev. Immunol.* 6:283 (1988)). Antibodies to MPG have been reported to block chemotactic and chemokinetic motility of cells (Herlyn, et al., *Ann. Rev. Immunol.* 6:283 (1988); de Vries, et al., *Int. J. Cancer* 38:465 (1986)). The anti-MPG antibodies cause the reduction of melanoma colony formation in soft agar (Harper, *J. Natl. Cancer Inst.* 71:259 (1983)).

Against this background of information and uncertain results, I have discovered anti-MEM136 antibodies that are clinical candidates for use in tumor immunotherapy.

SUMMARY OF THE INVENTION

In its broadest aspect, the present invention is directed to a novel anti-idiotypic antibody, antibody fragment, peptide, or antisera capable of reacting with at least one of the idiotopes: (a) murine monoclonal antibody MEM136 and derivatives thereof; (b) a monoclonal antibody having the same immunological specificity as antibody MEM136; or (c) polyclonal antibodies having the same immunological specificity as antibody MEM136, wherein (a), (b), or (c) is capable of reacting with a specific determinant (epitope) of a MPG antigen.

Additional aspects of the present invention include methods for using the novel anti-idiotype antibodies in active and passive immunotherapy, as well as the diagnosis, monitoring, and treatment of melanoma and other disease states associated with the epitope recognized by the MEM136 antibody.

BRIEF DESCRIPTION OF THE DRAWINGS

FIGS. 15A-15E depict the Ab1' response in sera of a representative mouse immunized with IMelpg2 or IM06 in MDP-A as assayed by IIF.

FIGS. 17A-17E show the IIF analysis of Ab1' anti-melanoma antibody in affinity purified rabbit Ab3.

DETAILED DESCRIPTION OF THE PREFERRED EMBODIMENTS

Figure 1:
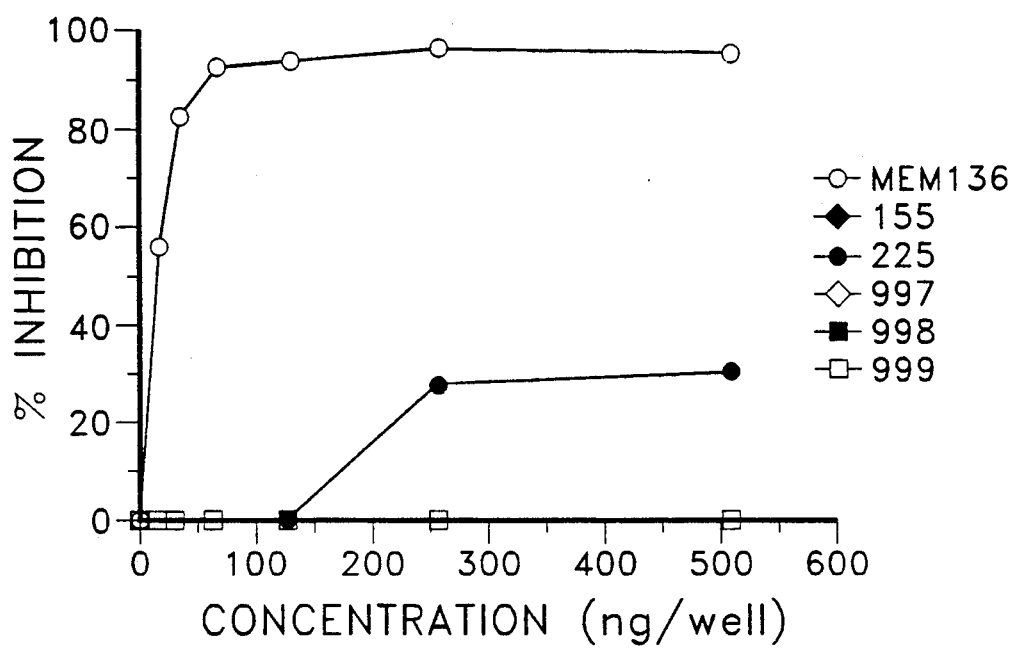
FIG. 1 depicts the fine specificity of Ab1s, in particular MEM136.

The following terms, as used in the disclosure and claims, are defined as follows:

"passive immunotherapy"—passive transfer of antibody to a patient or animal.

"active immunotherapy"—the induction of antibody and/or T-cell responses in a patient or animal.

"suppression"—the inhibition of an immune response or the inhibition of the expression of an idiotypic response.

"stimulation"—the induction of an immune response or the induction of the expression of an idiotypic response.

"tumor regression"—an overall 30% or greater reduction of tumor mass.

All of the references cited in this disclosure are hereby incorporated by reference.

As previously discussed, the potential for utilizing anti-idiotypic (anti-Id) antibodies to induce active anti-tumor responses in patients with neoplastic disease is enormous. I have explored the feasibility of using anti-Id antibodies (Ab2s) as immunoactivators to potentiate tumor-specific B and T cell responses in melanoma patients. Melanoma-associated chondroitin sulfate proteoglycan antigen (MPG) is synthesized and expressed by human melanoma cells. Proteoglycans are glycoproteins with glycosaminoglycan polysaccharide chains covalently attached to the serine residues in their core. The various biological properties of MPG in melanoma have been previously described. Briefly, MPG is involved in chemotactic and chemokinetic cell motility, and anti-MPG antibodies cause the reduction of melanoma colony formation in soft agar. MEM136 is a monoclonal antibody ("MoAb") which recognizes an epitope of undefined structure on the MPG molecule. When tested in an immunohistology study, MEM136 reacted to 80% of melanoma tissues, with minimal cross-reactivity to normal tissues. Therefore, an MPG epitope detected by MEM136 can serve as a potential tumor-associated antigen. Accordingly, as described below, I have (i) generated and characterized several site-specific anti-id antibodies; (ii) analyzed V-gene usage of select Ab2s by biochemical and immunochemical means, and (iii) screened the Ab2's for the ability to induce an anti-tumor response in small animals.

EXAMPLE 1

Development and Characterization of the Anti-idiotypic Monoclonal Antibody (IMelpg2) Directed to the Monoclonal Antibody MEM136 Directed Against MPG Antigen Materials and Methods The human melanoma cell line Colo38, obtained from Dr. Soldano Ferrone at New York Medical College, was grown in RPMI 1640 medium supplemented with 10% calf serum, 1% glutamine and 10 mg/ml of gentamycin sulfate. The anti-Id antibodies developed in connection with the present invention were produced by hybridomas generated from a fusion of splenocytes from A/J mice immunized with MoAb MEM136 and murine myeloma cell line SP2/0.

Monoclonal Antibodies

The MoAb MEM136 ($\gamma 1,\kappa$) (obtained from Hybritech, Inc., San Diego, Calif.) was purified on a protein A-Sepharose 4B column. MOPC21 ($\gamma 1,\kappa$) anti-idiotype antibody ("MOPC21") (available from Bionetics Lab Products, Charleston, S.C.) was used as an isotype-matched control for MEM136.

Preparation of F(ab')$_2$ Fragments

The concentration of MEM136 antibody solution in phosphate-buffered saline ("PBS") was adjusted to 1-2 mg/ml and the solution was dialyzed against 0.1M of citrate buffer pH 3.5. Pepsin was then added to give a final concentration of 25 µg/ml. The solution was incubated for 8 hours at 37° C. Thereafter, the reaction was stopped by increasing the pH to 8.0 by adding high salt protein A buffer. After cycling over protein A, the flowthrough that contained the F(ab')$_2$ portion of the molecule was collected and dialyzed extensively against PBS. The purity of the preparation was checked by examining its reactivity against heavy and light chain-specific antibodies in an ELISA.

Generation of Anti-MEM136 Idiotype Hybridomas

A/J mice were immunized three times with 100 μg of MEM136 coupled to keyhole limpet hemocyanin ("KLH") in incomplete Freund's adjuvant ("IFA") i.p. over a period of two months. Two weeks after the last injection, mice were boosted intravenous ("i.v.") with MEM136 antibody in PBS. Four days after this inoculation, the fusion was performed according to the methods described in Raychaudhuri, et al., *J. Immunol.*, 137: 1743–1749, 1986, with SP2/0 as a fusion partner and 50% polyethylene glycol, m.w. 1500. The hybrids were selected with HAT media.

Selection of Anti-MEM136 Idiotype Antibody (Ab2)

Initial screening of the hybridomas was carried out by ELISA in a binding assay with F(ab')$_2$ fragments of MEM136 and MOPC21. Wells containing antibody that bound to the MEM136 (F(ab')$_2$ fragment but not to the MOPC21 F(ab')$_2$ fragment were selected and additionally tested. The monoclonal anti-idiotope antibodies IM04 (γ1,κ), IM06 (γ1,κ), IM08 (γ1,κ), IM09 (γ1,κ), IM13 (γ1,κ), IM20 (γ1, κ), IM30 (γ2b,κ) and IMelpg2 (γ1,κ) were selected for further analysis.

Radioimmunoassay ("RIA")

Additional characterization of the Ab2s was done by RIA. Rabbit anti-mouse IgG was purchased from Southern Biotechnology Associates, Inc., Birmingham, Ala., and was radioiodinated as described in Raychaudhuri, et al., *J. Immunol.*, 137: 1743–1749 (1986). A binding assay was performed as described in Raychaudhuri, et. al., *J. Immunol.*, 137: 1743–1749 (1986). The F(ab')$_2$ fragments of either MEM136 or MOPC21 were added to PVC plates at a concentration of 100 to 200 ng/well. After overnight incubation at 4° C., the plates were blocked with 1% bovine serum albumin ("BSA") in PBS. Thereafter, varying dilutions of Ab2 culture supernatant were incubated at room temperature for 4 hours. The plates were developed using 10,000 counts of goat anti-mouse Ig in 100 μl of PBS containing 1% BSA. The binding site specificity of AB2s was determined by incubating Colo38 cells with $^{125}$I-MEM136 in the presence of varying concentrations of the Ab2s for 18 hours at 4° C. Thereafter, plates were washed and the counts bound to Colo38 were determined in a gamma counter.

Immunization of Rabbits

Adult New Zealand White ("NZW") rabbits (two per group) were immunized subcutaneously at different sites with 500 μg of unconjugated IM04 through IM30, and IMelpg2 in Syntex Adjuvant Formulation("SAF")-m adjuvant containing 250 jig of threonyl muramyl dipetide (threonyl "MDP") per rabbit. Rabbits were boosted with the same antigen concentration every 2 weeks and bled 7 and 14 days after each immunization. Each rabbit was immunized a maximum of four times. Control rabbits were immunized with 500 μg of MOPC21 or KLH alone.

Analysis of Anti-Anti-Idiotypic (Ab3) Response

The idiotypic responses induced by IM04, IM06, IM08, IM09, IM13, IM20, IM30 and IMelpg2 were analyzed by RIA. Briefly, 100 ng of MEM136-F(ab')$_2$ fragment was coated onto microtiter plates for two hours at room temperature. The plates were washed with PBS and then incubated with 1% bovine serum albumin (BSA) in PBS for one hour. Serially diluted sera from different experimental and control groups were incubated on the wells in the presence of 20,000 cpm of $^{125}$I-Ab2s for 18 hours. The plates were thoroughly washed and the radioactivity in each well was counted in a gamma counter. The results are expressed as percentages of inhibition of $^{125}$I-Ab2 binding to MEM136.

Isoelectric Focusing of Ab2s

Isoelectric focusing was performed using a pH 3-10 isoelectric focusing gel (Novex, Encinitas, Calif.). After fixing, the gel was destained with 10% acetic acid and 25% ethanol and then stained with the same solution containing 0.1% Coomassie Blue. pI standards were included to determine pH values (Pharmacia LKB Biotechnology, Piscataway, N.J.).

Idiotope Localization of Ab2 Antibodies

Immunoblotting assays were performed to determine whether or not the epitopes recognized by the anti-idiotypic antibodies were detected on isolated heavy or light chains of MEM136. Monoclonal antibody MEM136 was reduced with 5% 2-mercaptoethanol and its heavy and light chains separated in a 10% polyacrylamide-sodium dodecyl sulfate gel and transferred onto nitocellulose using a Transphor blotting apparatus (Hoefer, San Francisco, Calif.). As a positive control, unreduced MEM136 was run on the same gel. Control nitrocellulose strips were stained with Ponceau 5 Stain (Sigma Chemical Co., St. Louis, Mo.). Blots to be reacted with monoclonal anti-idiotypes were first blocked for 2 hours with BSA (3% in Tris-buffered saline). These blots were then incubated for 2 hours with $^{125}$I-labeled monoclonal anti-idiotype antibodies ($1 \times 10^5$ cpm/ml in blocking buffer). After washing several times with Tris-buffered saline, the blots were dried and analyzed by autoradiography.

Fine Specificity of Monoclonal Anti-MPG Antibodies

The binding of $^{125}$I-labeled MEM136 to the melanoma cell line Colo38 was examined in the presence of unlabeled antibodies MEM136, 225, 155, 997, 998, 999 and UPC10, an unrelated isotype-matched control antibody. Antibodies 225, 997, 998, and 999 were obtained from Dr. Soldano Ferrone, New York Medical College and the 155 antibody was obtained from Dr. J. Harper, Scripps Clinic and Research Foundation, La Jolla, Calif. A human melanoma cell line, Colo38, was grown in each well of 96-well plates. After fixation and blocking, the binding of $^{125}$I-MEM136 to Colo38 was determined in the presence of different concentrations of monoclonal anti-MPG antibodies 155, 225, 997, 998, and 999. As shown in FIG. 1, unlabeled MEM136 was the only antibody that was able to efficiently inhibit the binding of $^{125}$I-MEM136 to Colo38. Dose ranges of 8-16 ng of this antibody could inhibit the binding of $^{125}$I-MEM136 by 50%, while only 22–25% inhibition could be achieved with 225.28 at a concentration range of 256–512 ng, and no inhibition could be achieved with 155, 997, 998 and 999 at this concentration. From this data, I conclude that MEM136, 225.28, 155, 997, 998 and 999 detect distinct epitopes on the MPG molecule. Small amounts of inhibition seen with 225.28 could be due to steric hindrance contributed by high concentrations of 225.28 in the reaction mixture.

Monoclonal Ab2s Recognize an Idiotype on MEM136

Figure 2:
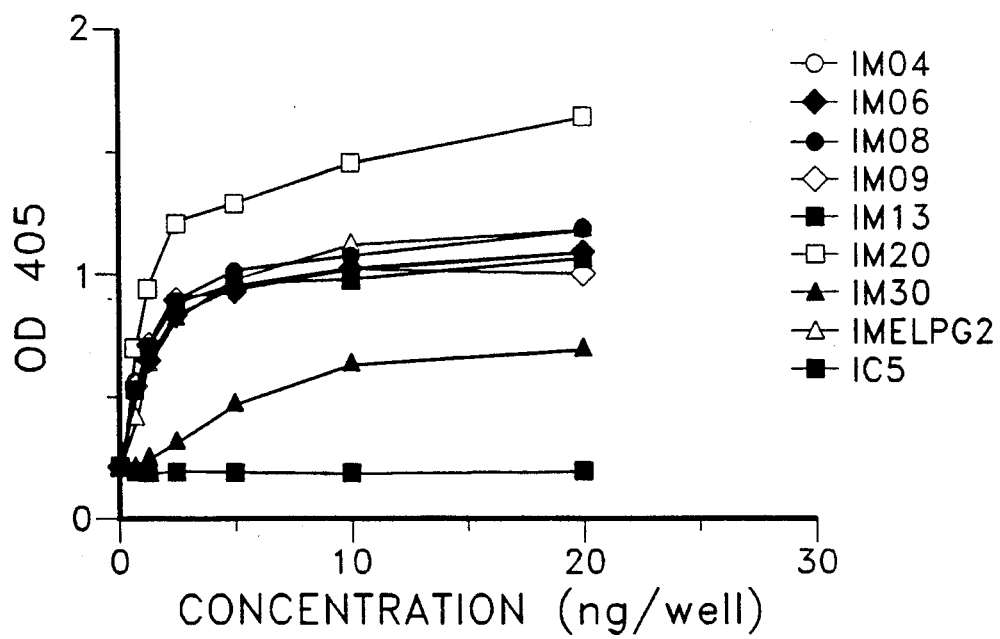
FIG. 2 illustrates that Ab2 binding is MEM136-F(ab')2-specific.
Figure 3A:
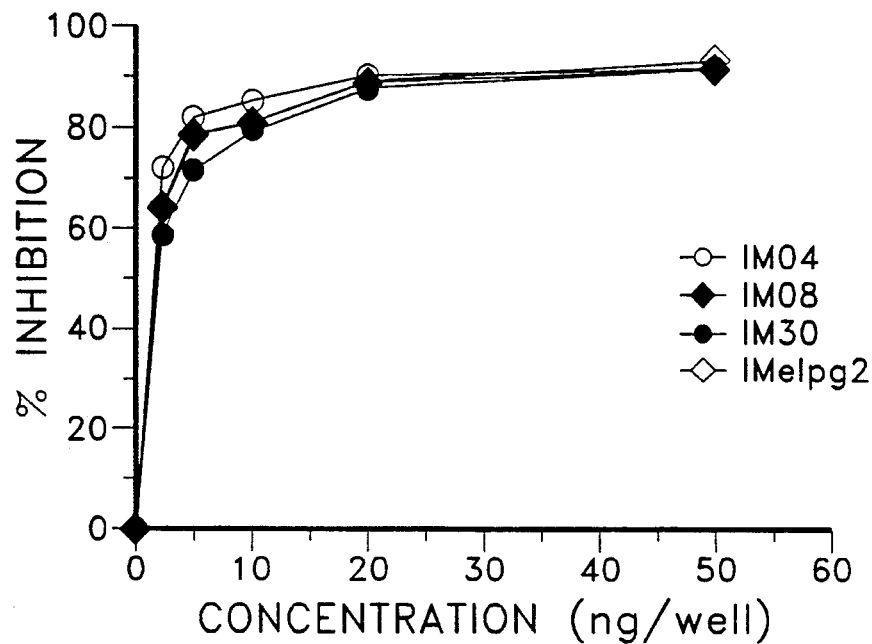
FIGS. 3A & 3B illustrate that the Ab2s are binding site idiotope-specific.
Figure 3B:
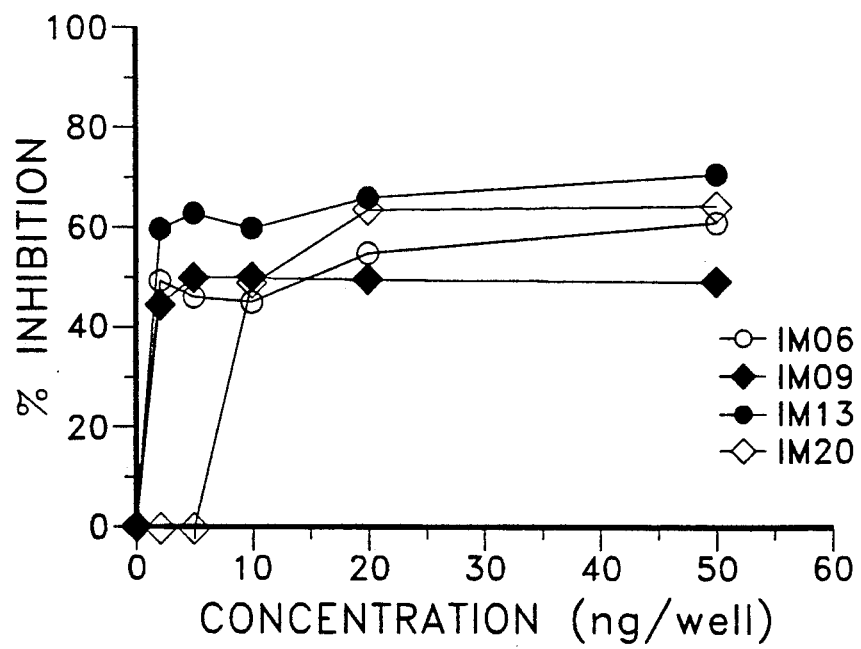

The hybridization of splenocytes from A/J mice immunized with MEM136 (γ1,κ) with SP2/0 cells yielded many hybridomas. The hybridomas IM04, IM06, IM08, IM09, IM13, IM20, IM30 and IMelpg2, which showed the highest binding activity with MEM136 and no binding with the isotype-matched control antibody MOPC21, were subcloned and ascites were produced in BALB/c mice. Various concentrations of different Ab2s (IM04 through IM30 and IMelpg2) were incubated with F(ab')$_2$ fragments of MEM136 coated onto each well of 96-well plates. After one hour of incubation, the plates were washed and developed with peroxidase-conjugated goat anti-mouse IgG. As control, various concentrations of an unrelated Ab2, IC5, were added. FIG. 2 shows the binding of different concentrations of these purified Ab2s to MEM136 -F(ab)$_2$ fragment.

To determine the site specificity of these anti-id antibodies, the binding of $^{125}$I-labeled MEM136 to Colo38 cells was determined in the presence of different Ab2s. The Ab2s could be divided into two distinct categories according to their inhibition capabilities. Group I, consisting of IM04, 08, 30 and IMelpg2, required <2 ng/well to inhibit the binding of $^{125}$I-labeled MoAb MEM136 to Colo38 by 50%. Group II, consisting of IM06, 09, 13 and 20, required a concentration of 50 mg/well to achieve a 45-70% inhibition of binding. This binding inhibition by Ab2s in groups I and II appears to be specific since Ab2s elicited by an unrelated MoAb did not affect the binding of MEM136 to Colo38. Graph 3A shows the inhibition of $^{125}$I-MEM136 binding to melanoma cells in the presence of different concentrations of IM04, IM08, IM30 and IMelpg2. Graph 3B demonstrates the same study in the presence of different concentrations of IM06, IM09, IM13 and IM20. A known concentration of IC5 was used as a control in both studies. Ten ng of IM04, IM08, IM30 and IMelpg2 inhibited the binding of $^{125}$I-MEM136 to tumor cells by 80-95%. With IM06, IM09, IM13 and IM20, 80% inhibition of binding was not achieved at any concentration. These results suggest that the idiotypes recognized by some Ab2s (group I) are closely related to the antigen combining site of MoAb MEM136. In the following experiments, IMelpg2 and IM06 were chosen to represent group 1 and group 2, respectively, for further characterization of these Ab2s.

Ab2 Recognizes a Private Idiotypic Determinant 136

Figure 4A:
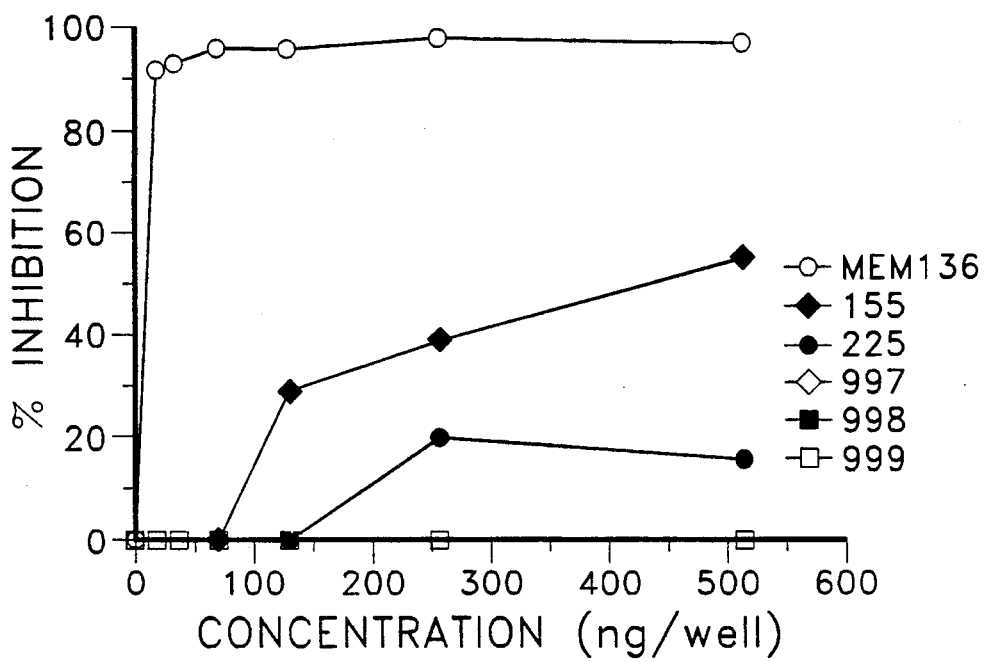
FIGS. 4A & 4B show that MEM136 was the only antibody that could effectively inhibit binding of $^{125}$I-Ab2 to MEM136.
Figure 4B:
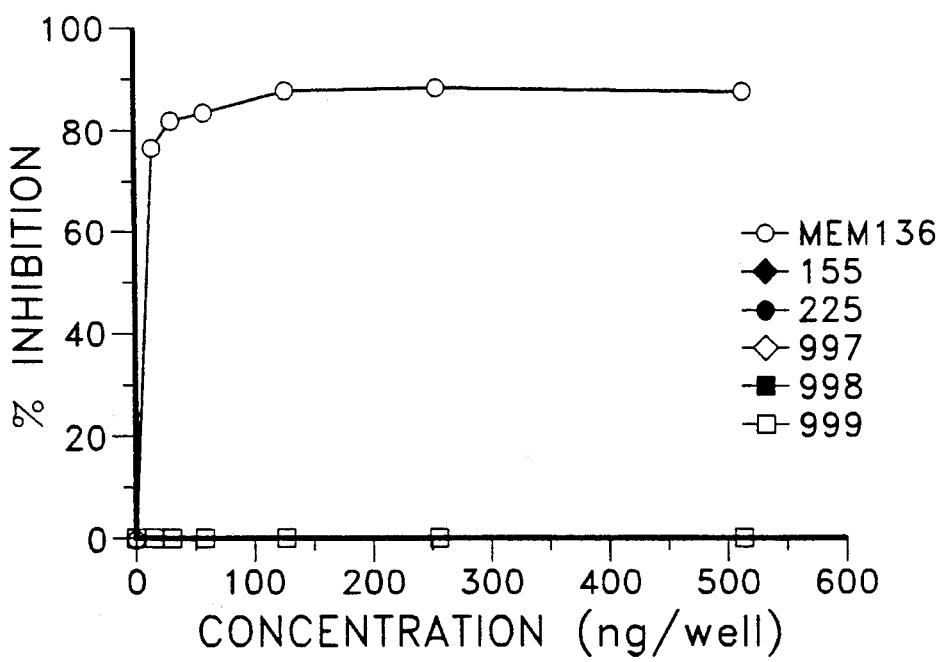

Idiotypic relationships among monoclonal anti-tumor antibodies MEM136, 155, 225.28, 996, 997 and 998 with IM06 and IMelpg2 were analyzed in a competition assay, where the binding of IM06 and IMelpg2 to MEM136 was determined in the presence of different Ab1s. As shown in FIGS. 4A & 4B, the MEM136 idiotope recognized by IMelpg2 may share determinants with 225 and 155 distantly(4A); and that the MEM136 idiotope recognized by IM06 does not share determinants with other Ab1s(4B). Microtiter plates were coated with MEM136 and incubated with $^{125}$I-IMelpg2 (4A) or $^{125}$I-IM06 (4B) overnight in the presence of different concentrations of MEM136, 155, 225, 997, 998 and 999. Thus, 100% inhibition of $^{125}$I-IMelpg2 binding to MEM136 could be achieved with 16 ng of MEM136, while 50% inhibition by antibody 155 required 400-500 ng/well. Similarly, 225.28 inhibited the binding of $^{125}$I-IMelpg2 to MEM136 by only 15-20% at a concentration of 250-500 ng/well. On the other hand, the inhibition of $^{125}$I-IM06 binding t 6 could be attained only with MEM136. These data confirm the premise that the Ab2s recognize an idiotope that may be present predominantly on immunizing MEM136.

Ab2s may Share a Determinant but Differ in their Fine Specificity

Figure 5A:
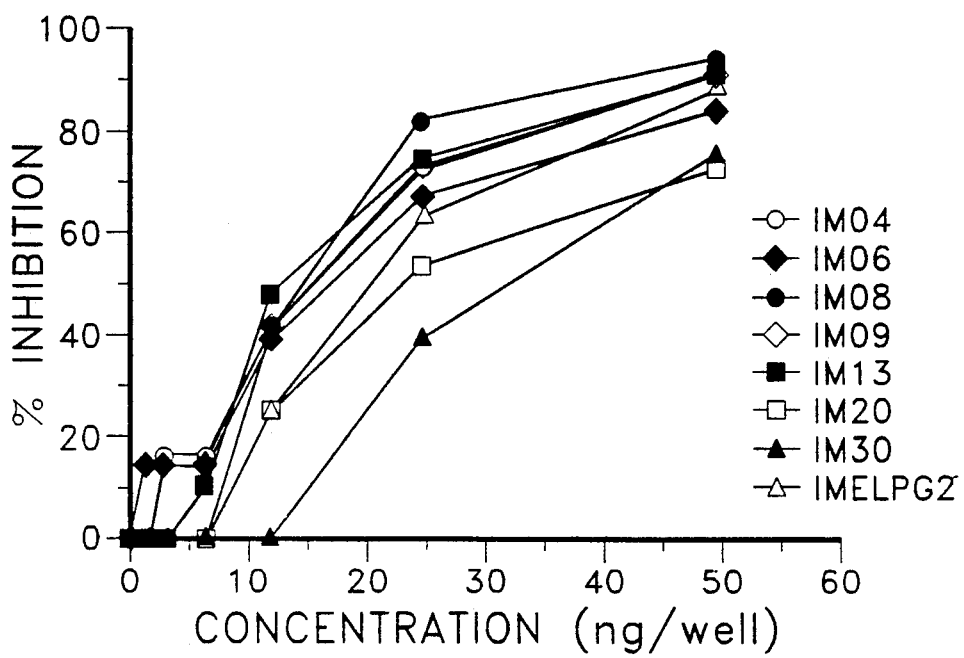
FIGS. 5A & 5B show the anti-MEM136 Ab2s could be grouped into two categories based on their inhibitory activity.
Figure 5B:
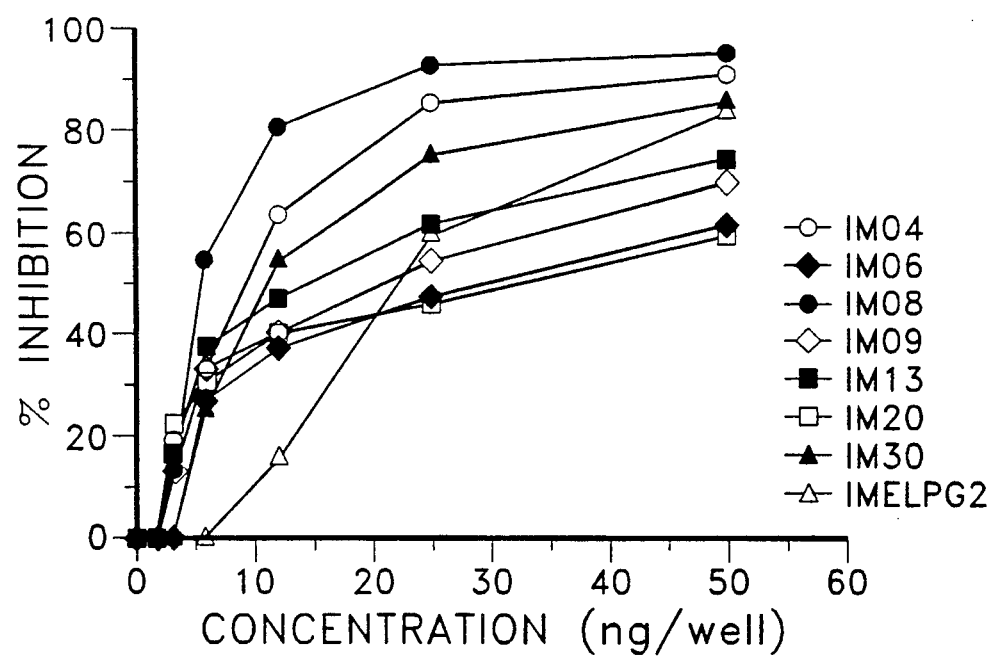

The spatial relationship of idiotopes recognized by IM04, 06, 08, 09, 13, 20, 30 and IMelpg2 was analyzed in a competition assay, where the binding of $^{125}$I-labeled IM06 or IMelpg2 to MEM136 was determined in the presence of different concentrations of cold Ab2s. As shown in FIGS. 5A & 5B, the differences in fine specificity of the Ab2s. Each well of polyvinyl plates was coated with 50 ng of MEM136 in PBS and incubated overnight at 4° C. Plates were blocked with 1% BSA in PBS for 1 hour and the inhibition of $^{125}$I-IMelpg2 (5A) and $^{125}$I-IM06 (5B) binding to MEM136 was studied in the presence of different 3.5 concentrations of various Ab2s. 5A: at 12 ng of different Ab2s, a range of inhibition of $^{125}$I-IMelpg2 binding to MEM136 of 0-50% was observed. 5B: at 12 ng of different Ab2s, a range of inhibition of $^{125}$I-IM06 binding to MEM136 of 16-80% was observed. When iodinated IMelpg2 was used as a ligand, 80-95% inhibition of $^{125}$I-IMelpg2 binding to MEM136 was achieved with 50 ng/well of IM04, 08, 30 and IMelpg2. At the same concentration, IM06, 09, 13 and 20 exhibited only 60-75% inhibition of $^{125}$I-IMelpg2 binding to MEM136. When IM06 was used as a radioligand, 50% inhibition of binding of $^{125}$I-IM06 to MEM136 was achieved with IM04, 06, 08, 09 and 13 at a concentration range of 12-16 ng/well. In the same inhibition assay, 50% inhibition of binding was achieved at a concentration range of 22-35 ng/well with IM20, 30 and IMelpg2. These results suggest that all Ab2s inhibited the binding of $^{125}$I-IM06 or IMelpg2 to MEM136 in a dose-dependent fashion. It appears, therefore, that the idiotope(s) recognized by these Ab2s are spatially linked or overlap with each other.

Analysis of the Variable Region of the Anti-Id MoAbs

Figure 6:
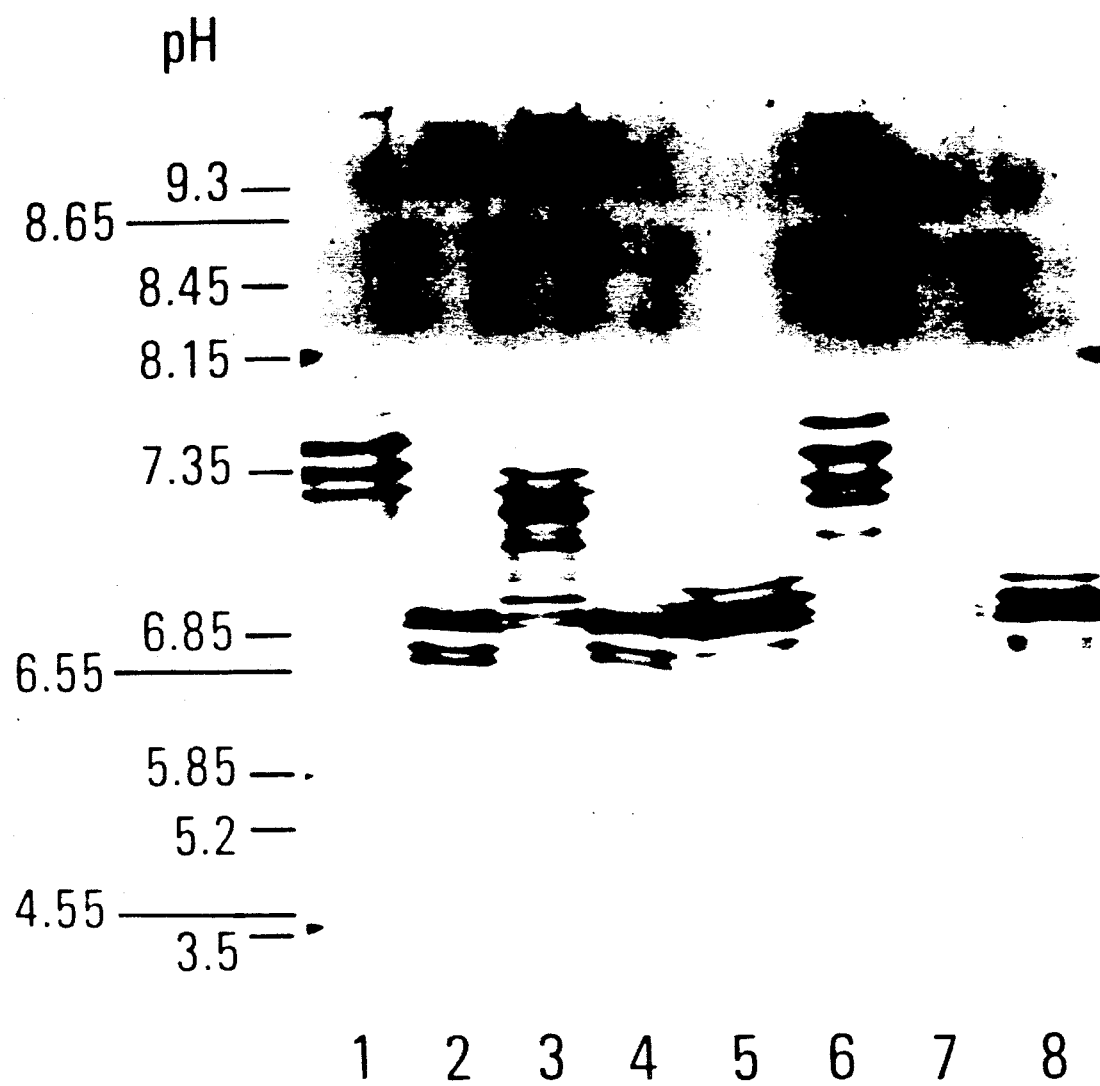
FIG. 6 depicts isoelectric focusing of anti-MEM136 Ab2s.
Figure 7A:
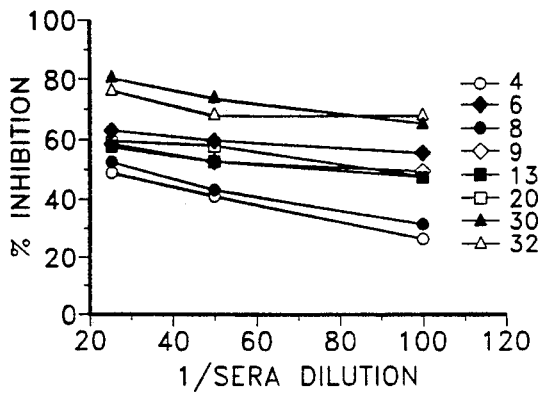
FIGS. 7A-H depict the inhibition by rabbit anti-anti-idiotypic antisera of the binding of $^{125}$I-Ab2s to MEM136.
Figure 7B:
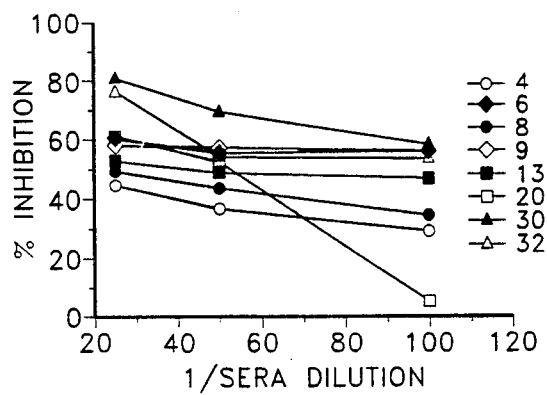
Figure 7C:
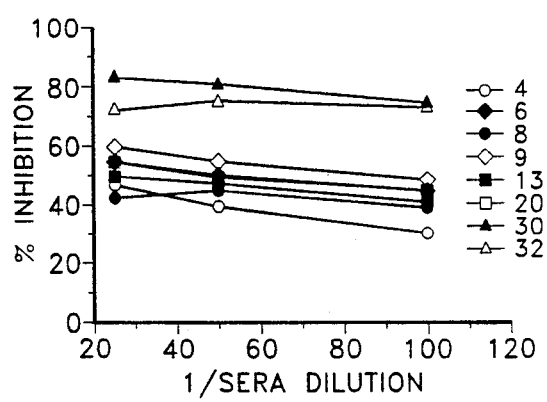
Figure 7D:
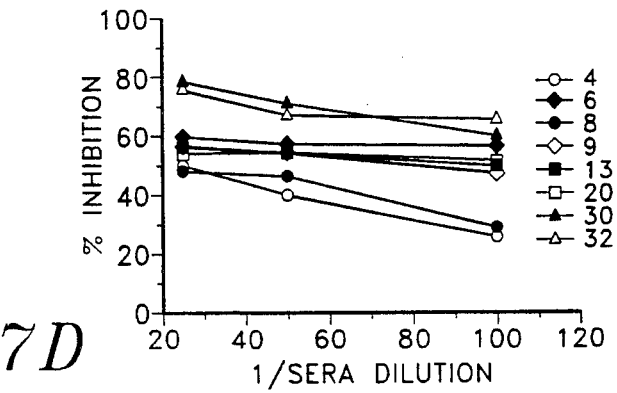
Figure 7E:
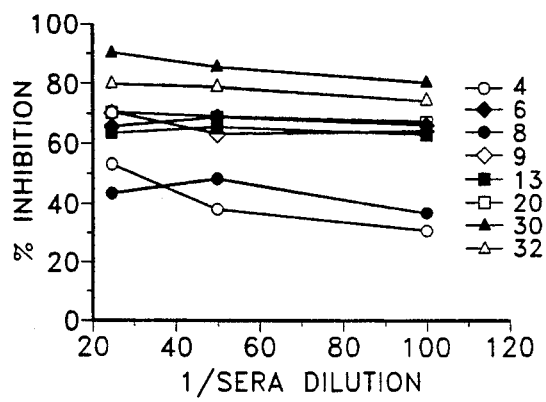
Figure 7F:
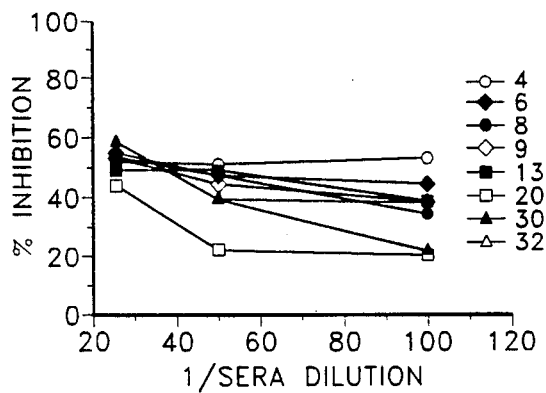
Figure 7G:
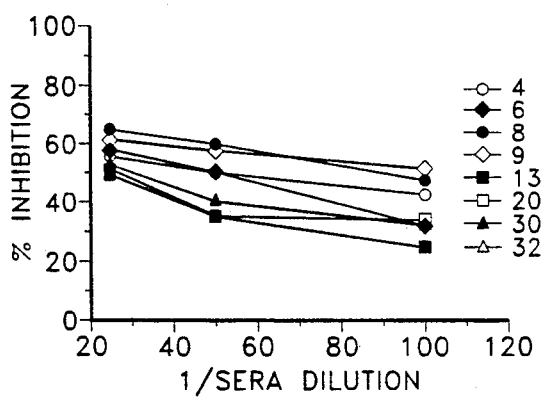
Figure 7H:
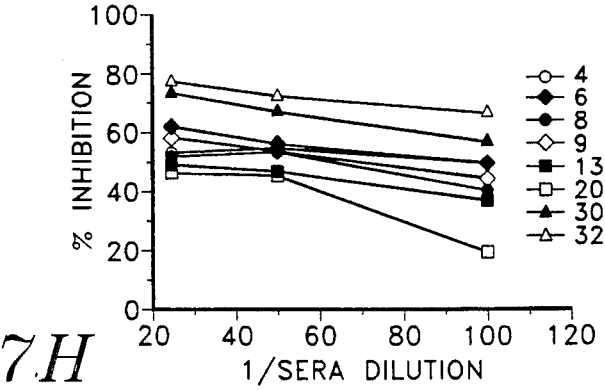

Immunochemical analysis was performed to determine the variability of the V-gene usage of the Ab2s. All eight Ab2s focused between pH 6.5-7.6 and comprised between 2-4 components. As shown in FIG. 6, the PIs of the monoclonal antibody Ab2s were determined using a pH 3-10 isoelectric focusing gel. Lane 1, IM04; lane 2, IM06; lane 3, IM08; lane 4, IM09; lane 5, IM13; lane 6, IM20; lane 7, IM30; and lane 8, IMelpg2. The spectrotype of each Ab2 was different, suggesting a difference in the variable region polypeptide sequence and/or carbohydrate moiety (FIG. 6).

Serological analysis was performed to corroborate the spectrotype analysis data. As mouse Ab2 immunized xenogenic antisera was analyzed, it is likely that an Ab2-induced idiotype response contributed by both framework and complementary determining region determinants was detected. Ab3 antisera elicited by IM04, IM06, IM08, IM09, IM13, IM20, IM30 and IMelpg2 were incubated with $^{125}$I-IM04 (6A), $^{125}$I-IM13 (6B), $^{125}$-IM30 (6C), $^{125}$-IM06 (6D), $^{125}$-IM20 (6E), $^{125}$I-IM04 (6F), $^{125}$I-IM08 (6G) and $^{125}$I-IMelpg2 (6H) on MEM136-coated microtiter plates. After overnight incubation, plates were washed and bound radioactivity was measured in a γ-counter. As shown in FIG. 7, each antiserum containing anti-anti-idiotype antibodies (Ab3) inhibited the binding of the corresponding anti-Id MoAb to a different extent. The Ab3s induced by IM30 and IMelpg2 inhibited the binding of $^{125}$I-IM04, -IM06, -IM13, -IM20, -IM30 and -IMelpg2 to the MEM136-F(ab')$_2$ fragment most efficiently. The binding of $^{125}$I-IM04 and -IM08 to MEM136 could not be competed by IM30 and IMelpg2 induced Ab3s as effectively as the Ab3s induced by IM04, 08 and 13. The hierarchy of inhibition of binding of 125I - IM 06, 09, 13, 20, 30 and IMelpg2 binding to MEM136 by Ab3 sera induced by different Ab2s can be ranked as follows; IM30 and IMelpg2>IM06, 09, and 20 >IM04 and IM8. On the other hand when binding of $^{125}$I-IM04 and IM08 to MEM136 MoAb1 is considered, IM04, 08 and 13 induced Ab3 sera demonstrated highest inhibitory activity. These results suggest that the Ab2s can be grouped into at least three categories based on their immunogenicity and the ability to induce anti-anti-idiotypic antibodies. If the differential reactivity patterns of the antisera do not reflect variability in immune responses of immunized rabbits, the idiotypes expressed by the eight Ab2s differed in their immunogenicity.

Immunoblotting of MEM136 using Monoclonal Anti-Idiotypes

Figure 8A:
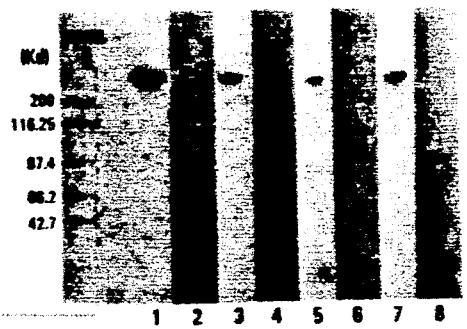
FIGS. 8A, 8B and 8C show idiotope localization of anti-MEM136 Ab2 antibodies.
Figure 8B:
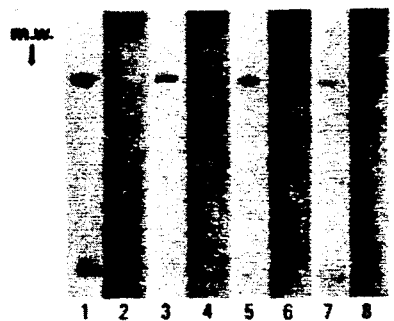
Figure 8C:

Idiotypes may be present on the isolated heavy or light chains of immunoglobulins or result from the association of both chains (See, FIG. 8). Monoclonal antibody MEM136 was reduced with 2-mercaptoethanol and its heavy and light chains separated in a 10% polyacrylamide-sodium dodecyl sulfate gel and transferred onto nitrocellulose. As a positive control, unreduced MEM136 was run on the same gel. The blots were then incubated with $^{125}$I-Ab2 antibodies and analyzed by a autoradiography. To determine the identities of the idiotypes for the monoclonal anti-idiotypes, MEM136 was reduced and its heavy and light chains were electrophoretically separated and transferred onto nitrocellulose. Of the nine anti-idiotype antibodies tested, none reacted with isolated heavy or light chains (FIG. 8). As a positive control, when MEM136 was electrophoretically resolved and blotted under non-reducing conditions, all nine anti-idiotypic antibodies showed strong reactivity (FIG. 8). While all nine anti-idiotypic antibodies were unreactive with isolated heavy or light chains, the possibility remains that an idiotope present on a single chain could have been destroyed by reduction with 2-mercaptoethanol. This consequence seems unlikely, however, since single-chain idiotypes are usually unaffected by 2-mercaptoethanol. The melanoma-associated proteoglycan molecules are believed to play many important roles in potentiating metastatic properties of melanoma. During the process of invasion and metastasis, it is necessary for tumor cells to traverse the extracellular matrix (ECM). The basement membranes within the ECM are composed mainly of collagen type IV meshed laminin, entactin, fibronectin and proteoglycans. A substantial body of evidence exists to suggest a close correlation between extracellular membrane degradation and tumor cell invasion and metastasis. Therefore if tumor cells are prevented from binding to the ECM, metastasis may be inhibited. To this end, a humoral response can be induced against MPG to develop antibodies which will act as antagonists and interfere with the binding of melanoma cells to the basal lamina or the basement membrane.

An antibody response can be induced against a tumor antigen by the use of anti-idiotype antibodies made against a monoclonal or polyclonal antibody directed against epitope(s) present on the tumor-associated antigen. The advantages of such an approach have been stated elsewhere (Kennedy, et al., Biotechniques 3:4040 (1985); Herlyn, et al., *Science* 232:100 (1986); Raychaudhuri, et al., *J. Immunol.* 137:1743 (1986)). has described the development and characterization of anti-idiotype antibodies ed against a monoclonal anti-human MPG antibody, MEM136. has selected monoclonal anti-idiotype antibodies IM04, 06, 08, 09, 13, 20, 30 and IMelpg2 based on their binding capability to immunizing MEM136 relative to an isotype matched control antibody. The antibodies IM04, 08, 30 and IMelpg2 (group 1) almost completely inhibited the binding of MEM136 to the human melanoma cell line Colo38 at a concentration of 10–20 ng/well. The antibodies IM06, 08, 13 and 20 (group 2), on the other hand, only inhibited the binding of MEM136 to Colo38 by less than 70%, even at a concentration of 50 ng/well. Thus, the Ab2 antibodies in group 1 have a much higher idiotope site specificity than those in group 2. A more detailed characterization was performed on antibodies IMelpg2 and IM06 were considered as representative Ab2s from group 1 and group 2 respectively for detailed characterization of other Ab2s. The spatial relationship of idiotopes recognized by the Ab2s was analyzed in a competition assay, where the binding of $^{125}$I-IMelpg2 and IM06 to MEM136 was determined in the presence of different Ab2s. Antibodies IM04, 08, 30 and IMelpg2 (group 1) inhibited the binding of $^{125}$I-IMelpg2 to MEM136 by 100% at a concentration of 50 ng/well. At the same concentration, IM06, 09, 13 and 20 inhibited IMelpg2 binding to MEM136 by only 60–75%. However, when $^{125}$I-IM06 was used as a ligand, there was no clear cut relationship between the percent inhibition of 1251 IM06 binding to MEM136 and the site specificity of the Ab2s. These data indicate that the idiotope(s) recognized by the different Ab2s overlap.

Spectrotype analysis demonstrated differences in the isoelectric point ("PI") of the different Ab2s. Immunochemical analysis was corroborated with serological data by analyzing the ability of Ab2-induced antisera to inhibit the binding of 1251 Ab2s (IM04 through IMelpg2) to MEM136. As demonstrated in FIG. 6, the Ab2s were immunologically distinct. Based on the cross-reactivity study, the Ab2s were grouped into three categories. IM30 and IMelpg2 immune sera (group 1) induced an immunologically similar anti-anti-idiotype (Ab3) response and most effectively inhibited the binding of $^{125}$I-IM06, −09, −13, −20, −30 and IMelpg2 to MEM136. IM04 and 08 immune sera (group 2) only minimally inhibited the binding of the above $^{125}$I-Ab2s to MEM136. IM06, 09 and 20 immune sera (group 3) inhibited binding of $^{125}$I-IM06, −08, −09, −13, −20, −30 and IMelpg2 to MEM136 at an efficiency intermediate to groups 1 and 2. The binding of $^{125}$I-IM04 and −08 to MEM136, on the other hand, was most inhibited by immune sera from IM04 and IM08, respectively, while IM30 and IMelpg2 immune sera inhibited the same binding minimally. This data indicates that though IM04, 06, 30 and IMelpg2 are all site-related, they are immunologically distinct.

Finally, in an attempt to localize the idiotope on the Ab1, MEM136 (Ab1) was run on SDS-PAGE gels under reducing and non-reducing conditions, blotted onto nitrocellulose and subsequently probed with $^{125}$I-Ab2s. In all cases the idiotope was located only on the native molecule.

To summarize, the data indicate that a library of both site-related and site-unrelated Ab2s has been generated which are immunologically distinct. The next step in selecting an therapeutic candidate involves determining which of these anti-idiotype antibodies is best able to induce a tumor-specific humoral response.

EXAMPLE 2

Assay Evaluation of IM06 and IMelpg2

Antibodies raised against melanoma proteoglycan epitopes have been shown to inhibit cell adhesion reactions and matrix driven chemotaxis. This leads directly to the consideration of their potential ability to interfere with melanoma:matrix interactions required for malignant tumor cell invasion and metastasis. Preliminary experiments on invasion of matrices can be conveniently and relatively cheaply carried out in culture. Tissue culture experiments are also useful in defining the mechanisms of any observed inhibition of cellular invasion. Increased cell surface expression of melanoma proteoglycans in cells cultured from invasive stages of melanoma, the shedding and incorporation of this material into the extracellular matrix and the demonstration of similar material in the matrix surrounding endothelial cells in early invasive stages of neovascularization are all observations which support the link of these proteoglycan epitopes with cellular invasion. The antibodies under consideration could block cell:matrix interactions in at least two ways: a) by binding to a cell membrane site, inhibiting its interaction with a matrix site; and b) by binding to a matrix site, inhibiting its interaction with a cell membrane site. If these antibodies are important in interfering with tumor cell invasion and metastasis, this could explain anti-tumor activity in the absence of immune targeting, and is of clear clinical importance.

DESCRIPTION OF THE IN VITRO ASSAYS

(1) General considerations

Invasion of biological structures by tumor cells takes place over relatively long time frames, and the number of invading cells in a population is very small. These considerations place definite constraints on the assays. Exposure to different matrix components will affect not only invasion, but also proliferative rate and gene expression. In practice, I have adjusted for this proliferation that may take place during an invasive assay but ignored changes in gene expression. Determining the number of invading cells using radioisotopic labeling of the tumor cells yields high experimental variations due to the long duration of the assays (days), differential proliferation rates and the small percentage of the labeled population which will actually invade. Most of these assays are best quantitated by direct visualization and counting of the invading cells. This is tedious but unavoidable.

(2) Invasion of transwell barriers impregnated with EHS-derived basement membrane matrix (matrigel)

In this assay a double chamber system is used. Separating the two chambers is a polycarbonate filter with eight micron pores. Corning "Transwells" were used for this assay as these are much simpler to handle than a Boyden chamber. They consist of 24-well tissue culture plates with removable inserts. The bottom of the insert consists of the polycarbonate filter and the test cells are plated on top of this. 100 $\mu$l of a 1:20 dilution of commercial Matrigel (Collaborative Research Inc.) is added to the insert on top of the filter. This is allowed to impregnate the filter and to gel, and is then dried down until use. When required, the matrigel is rehydrated for two hours with serum-free medium. $5 \times 10^4$ test tumor cells are added to the upper well in 200 $\mu$l of medium. 0.8 ml of medium is added to the lower chamber. The transwells are incubated for 2 to 7 days to allow for the tumor cells to invade through the matrix in the filter and so reach the lower chamber. The exact time required depends on the cell line and must be determined in control experiments. The cultures are fed daily during this time. The upper inserts are then removed and the cells in the lower chamber allowed to grow up to form colonies over the next week. The plates are then washed, fixed in methanol and stained with acid Hematoxylin. The small number of cells invading through the matrix-impregnated filter is essentially clonal, and results from colony counting are identical to those using radiolabeled cell populations. Colony counts are much more reproducible and have lower experimental errors. The number of cells plated in the upper chamber at the start of the experiment does not allow for any extensive proliferation (it is a very small area), and proliferation of cells in the upper chamber is excluded as a meaningful variable. Test antibodies are included in the medium in both chambers until the insert (upper chamber) is removed. At the time that the initial cells are plated, aliquots of cells are also plated in each test medium to look for any unexpected toxicity. These cells are monitored for the time that the upper chambers are in place.

TABLE 1

Effect of Different Ab2s on tumor Cell Invasion

| Medium | Number of Colonies (invaded cells) % of Control |
|---|---|
| Control Antibody (MOPC21) | 100 |
| IM04 | ND |
| IM06 | 18 |
| IM08 | 190 |
| IM09 | 220 |
| IM13 | 134 |
| IM19 | 344 |
| IM20 | 228 |
| IM30 | ND |
| IMelpg2 | 35 |
| MEM136 | 40 |

ND = not done.

INDUCTION OF AN Ab3 RESPONSE IN RABBITS

Figure 9:
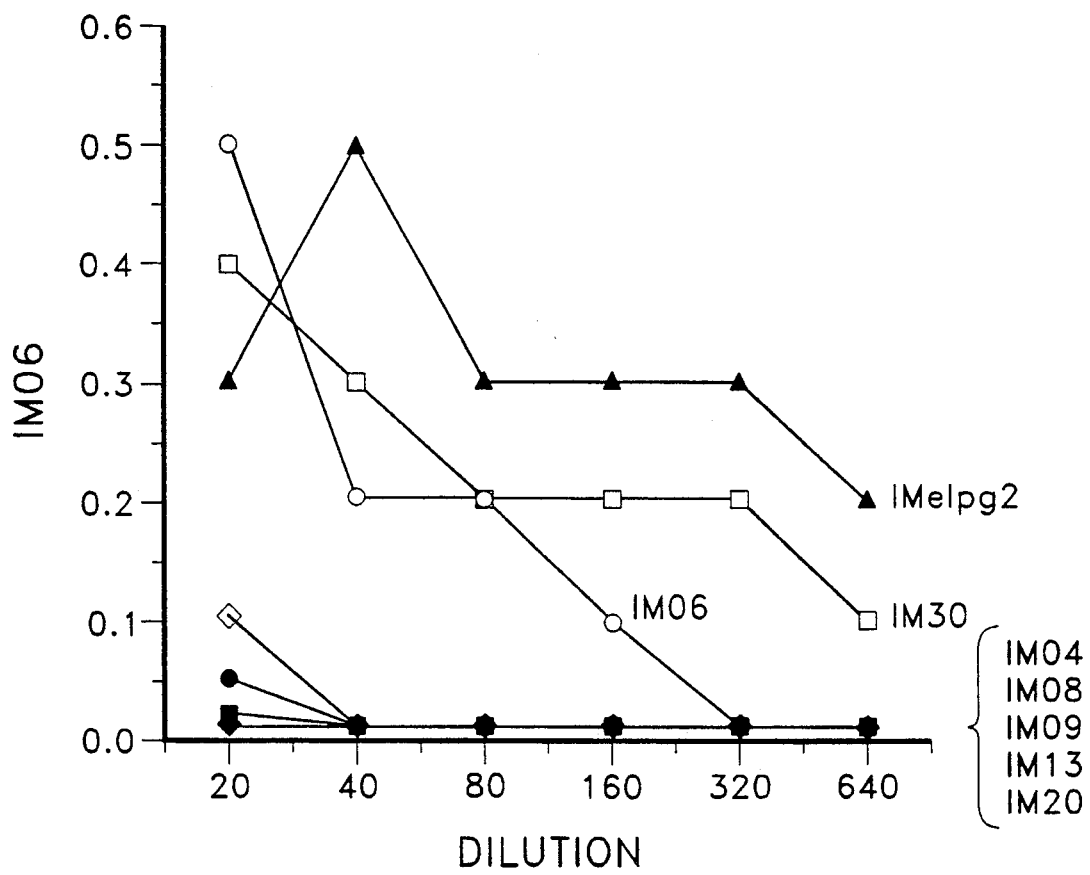
FIG. 9 depicts the Ab3/Ab1' response in rabbits immunized with the panel of Ab2s.
Figure 10A:
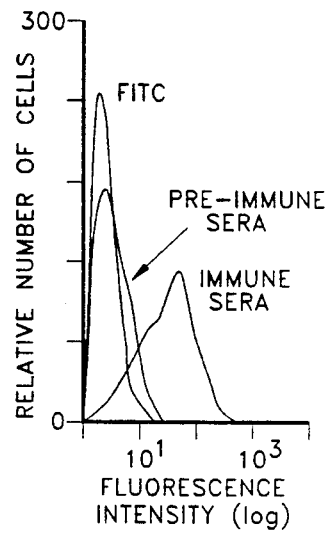
FIGS. 10a-10e show the Ab1' response in sera of rabbits immunized with IMelpg2 or IM06 in MDP-A as determined by IIF analysis.
Figure 10B:
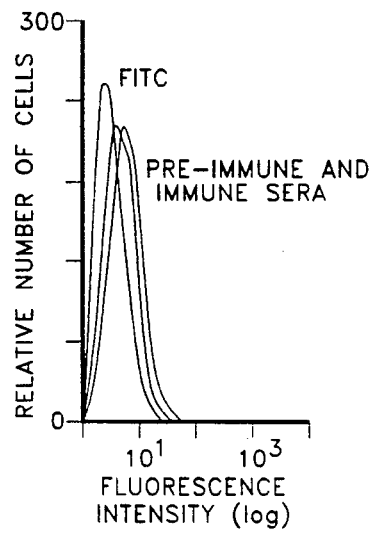
Figure 10C:
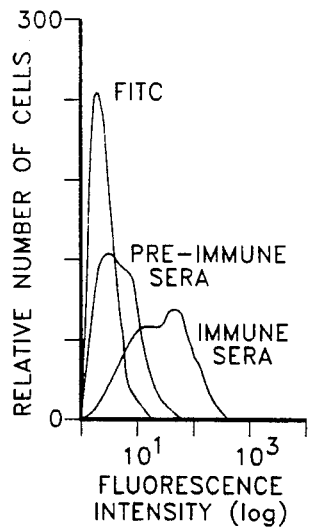
Figure 10D:
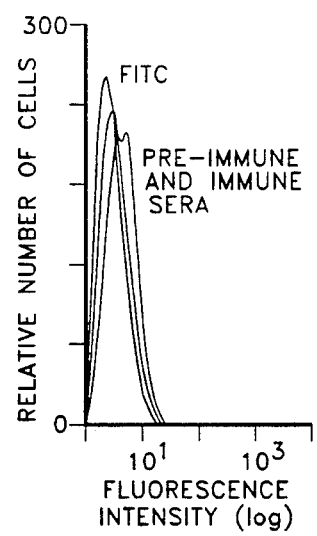
Figure 10E:
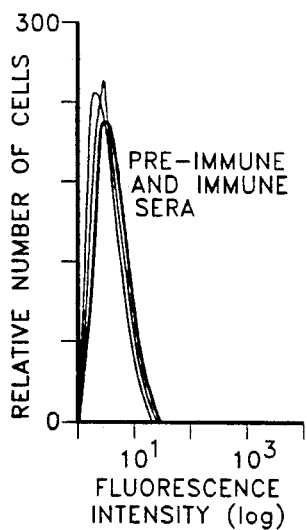

The anti-tumor humoral response induced by different Ab2s in rabbits was studied against a melanoma cell line, Colo3g, which expresses MPG. Unrelated isotype-matched control antibody immune rabbit sera was used as a control. FIG. 9 demonstrates that after two immunizations all the Ab2s were able to induce an anti-anti-idiotype response in rabbits. I then investigated whether any of the sera contained anti-tumor antibodies. Serial dilutions of Ab2 immune sera were incubated for 1 hour with Colo38 cells grown in each well of 96-well plates. The plates were finally developed with goat anti-rabbit IgG. FIG. 9 shows representative binding data with Ab2 immune sera. As demonstrated, only IM06, IM30 and IMelpg2 induced an anti-tumor response after two immunizations. The binding was specific as the sera did not bind to control MPG-neuroblastoma cell line NMB7. The control sera also did not show appreciable binding to Colo38. Sera collected from rabbits after third and fourth immunizations contained more anti-tumor antibodies than sera collected after the second immunization.

The data in Table 1 describes the effect of different Ab2s on tumor cell invasion. The results are expressed as a percentage of control colonies invaded. For example, with IM06 only 18% of the control colonies were formed, i.e., there was an 82% inhibition of colony formation. In contrast, 65% inhibition was achieved with IMelpg2. The data demonstrates that both IM06 and IMelpg2 are interfering (via MPG determinant) with the interactions between tumor cells and the basement membrane component that is needed for tumor cell invasion and metastasis. It is possible that IM06 and IMelpg2 bear the MPG image and act as an antagonist for cell and basement membrane interaction. When a direct binding ELISA was performed to determine the presence of anti-MPG antibodies in rabbit sera induced by various Ab2s, it was observed that IMelpg2 induced the highest level of Ab3(Ab1') response. See FIG. 9.

EXAMPLE 3

In Vitro Evaluation of IMelpg2 and IM06 in Rabbits and Mice

Cells

The human melanoma cell lines Colo38, 297, Meljur and M21 (MPG+) were grown in RPMI 1640 medium supplemented with 10% calf serum, 1% glutamine and 10 µg/ml gentamicin sulfate. The human neuroblastoma cell line NMB7 and the mammary carcinoma cells MCF7 (MPG−) were grown in the same media and used as control cell line. The Colo38 cell line is available from Dr. Soldano Ferrone at New York Medical College. Other cell lines were obtained from ATCC, Rockville, Md.

mAb and conventional antisera

The MoAb1 MEM136 ($\gamma$1,$\kappa$) is reactive with a MPG epitope. The MoAb1 225.28 ($\gamma$2a,$\kappa$) is reactive with a different epitope on MPG than that recognized by MEM136, (Wilson et al., Int. J. Cancer 28:293 (1981)). The mAb MOPC21 ($\gamma$1,$\kappa$; Bionetics, Charleston, S.C.) was used as an isotype-matched control. The mAb2s, IM04, IM06, IM08, IM09, IM13, IM19, IM20 and IMelpg2, are secreted by hybridomas generated from splenocytes from A/J mice immunized with MEM136. Anti-HLA class I mAb TP25.99 and anti-HLA class II mAb 05/13 were kindly provided by Dr. S. Ferrone of New York Medical College. The MoAb1 MEM136 ($\gamma$1,$\kappa$) was purified on a protein A-Sepharose 4B column, as were all Ab2s. The purity of these preparations was tested by SDS-PAGE electrophoresis and was >95% as judged by Coomassie blue staining. Immunoreactivity was tested in an ELISA. For RIAs, MoAbs were labeled with $^{125}$I utilizing the chloramine T method. FITC-goat anti-mouse IgG antibodies and FITC-goat anti-rabbit IgG antibodies were purchased from Becton-Dickinson, Mountain View, Calif.

Immunization of mice

Eight wk old BALB/C mice (Jackson Labs., Bar Harbor, Me.) (three in each group) were immunized with 50 µg of IM06 or IMelpg2 emulsified with MDP-A. MDP-A is an adjuvant containing a muramyl dipeptide derivative (Allison, et al., J. Immunol. Methods 95:157 (1986)). Mice were injected in the footpads, tailbase and multiple subcutaneous ("s.c.") sites. Three subsequent immunizations were given s.c. with the same dose of antigen at 2-wk intervals. Control mice were immunized with 50 µg of MOPC21, an unrelated isotype-matched antibody, with MDP-A. A group of mice were also immunized with $10^7$ MFG-0 Colo38 cells or $10^7$ MPG- NMB7 cells. Mice were bled 7 and 14 days after each immunization.

Immunization of rabbits

Adult NZW rabbits were immunized subcutaneously (s.c.) with 500 µg of Ab2s with MDP-A. Rabbits were boosted three times with the same amount of antigen every 2 wks and bled 7 and 14 days after each immunization. Control rabbits were immunized with 500 µg of MOPC21 with MDP-A. A group of rabbits were also immunized with $10^7$ Colo38 or $10^7$ NMB7 cells.

Serological assays

Indirect immunofluorescence ("IIF") was performed by incubating target cells (5×10$^5$ cells in PBS supplemented with 0.2% BSA and 0.02% NaN$_3$) with dilutions of antisera or purified antibodies for 1 hour at 4° C. After incubation, cells were washed and incubated with FITC-labeled anti-IgG. Thereafter, cells were washed and analyzed on a FACScan (Becton Dickinson).

Radioimmunoassays

The inhibition assay to map determinants recognized by different antibodies was performed by adding $^{125}$I-MEM136, mixed with different amounts of unlabeled antibody without prior incubation, to Colo38 melanoma cells fixed on microtiter plates. After overnight incubation at 40° C., plates were washed and bound radioactivity was counted in a gamma counter. The specificity of the inhibition was analyzed by measuring the ability of test sera to inhibit the binding of $^{125}$I-MEM136 to Colo38 cells. Results are expressed as percent of inhibition of binding of MEM136 to MPG+ Colo38 cells in presence of control or immune sera as compared to the binding performed in the presence of preimmune sera.

The idiotypic response was analyzed as described earlier (Raychaudhuri, et al., J. Immunol. 139:1743 (1987)). Briefly, 100 ng F(ab')$_2$ fragments of IM06 or IMelpg2 were bound to microtiter plates for two hours at room temperature. The plates were washed with PBS and then incubated with 1% BSA in PBS for one hour. Serially diluted sera from the different experimental and control groups were incubated in the wells simultaneously in the presence of 10,000 cpm of $^{125}$I-MEM136 for 18 hours at 40° C. The plates were thoroughly washed and the radioactivity in each well was determined with a gamma counter. The results are expressed as percentages of inhibition of $^{125}$I-MEM136 binding to the Ab2-F(ab')$_2$ fragment in presence of control or immune sera, as compared to the binding performed in the presence of preimmune sera.

Affinity Determination

Dissociation constants were determined by performing the Scatchard analysis of equilibrium binding of $^{125}$I-MEM136 to different Ab2s according to the procedure of Wilson and Lentz, Biochemistry, 27:6667 (1988). Briefly, wells of 96-well plates coated with Ab2s (100 ng/well) were incubated with different concentrations of $^{125}$I-MEM136 for 18 hours at 4° C. After incubation, an aliquot of the $^{125}$I-MEM136 solution was removed and placed in a gamma counter to determine the amount of free 125I-MEM136. The plates were then washed and dried and the amount of bound $^{125}$I-MEM136 per well was determined.

Affinity purification of Ab3 antibodies

Immune rabbit sera, diluted (1:5) in borate buffered saline ("BBS", pH 8.0), were first passed through an adsorbent containing bound normal mouse IgG to eliminate the anti-isotypic antibodies. Sera were subsequently applied to an Ab2-Sepharose 4B affinity column. The bound antibodies were eluted with 0.1M acetic acid containing 150 mM sodium chloride and the eluates neutralized immediately. These anti-anti-idiotypic antibodies (Ab3s) were examined for their ability to bind to Colo38 cells. As control, sera from rabbits immunized with MOPC21 were purified on MOPC21-Sepharose 4B column.

Ab3 specificity assays

Purified Ab3s were incubated with Colo38 (MPG+) and NMB7 (MPG−) cell lines as described (Jensen, P. E., J. Exp. Med, 171:1779 (1990)). Briefly, Colo38 and NMB7 cells were fixed with 1% paraformaldehyde for 30 min. at room temperature and washed thoroughly. The purified Ab3 (100 μg) was incubated with these fixed Colo38 and NMB7 cells (100×10$^6$) for 2 hours at room temperature. The degree of absorption was determined by IIF analysis on Colo38 cells using Ab3s before and after absorption with Colo38 and NMB7 cells.

To determine the cross-reactivity of IMelpg2-Ab3 (Ab3 purified from IMelpg2 immune rabbit sera) with IM06-Ab3 (Ab3 purified from IM06 immune rabbit sera), IMelpg2-Ab3 was absorbed on IM06-Sepharose 4B absorbent. After absorption, both bound and unbound fractions were tested for anti-melanoma and anti-idiotypic activity. For the determination of Ab1' reactivity, various fractions were analyzed in IIF and also inhibition of $^{125}$I-MEM136 binding to Colo38 was determined in the presence of various fractions. Anti-idiotypic reactivity was determined as described earlier. Different concentrations of Ab3 purified from different rabbits (IM06 and IMelpg2 immune rabbit sera) were incubated with $^{125}$I-IMelpg2-Ab3 (60,000 cpm/well) in IMelpg2-F(ab')$_2$ coated (100 ng/well) plates for 18 hours at 40° C. The same technique was employed to analyze different dilutions of mouse sera. The plates were washed, dried and counted in a gamma counter. For the determination of the Ab1' cross-reactivity, the binding of $^{125}$I-IMelpg 2-Ab3 to Colo38 was measured in the presence of the same fractions described above.

Induction of Ab3 response in rabbits

The goal of this study was to identify a mouse Ab2 which would induce an anti-MPG response across the species barrier and react with MPG+ melanoma cells. I examined the induction of Ab3 and Ab1' responses in rabbits by different monoclonal Ab2s generated against MEM136. Table 2 describes the name, isotype and relative affinity of different Ab2s. The anti-tumor humoral response induced by different Ab2s with MDP-A in rabbits was assessed using the MPG-positive melanoma cell line, Colo38. As a control, rabbits received an isotype-matched control antibody, MOPC21. After two immunizations, all Ab2s induced Ab3 responses in rabbits. However, only sera from rabbits immunized with IM06 and IMelpg2 produced significantly higher binding to melanoma cells compared to the binding observed with isotype matched MOPC21 immune sera. The binding was specific as the sera did not bind to a control neuroblastoma cell line, NMB7.

TABLE 2

Characteristics of Ab2s used in this Study

| Name of Ab2 | Isotype | Relative Affinity to MEM 136[a] | IC$_{50}$[b] of MEM136 binding to melanoma cells |
|---|---|---|---|
| IM04 | Y1,κ | 1.01 × 10$^{-10}$ | 1 μg/ml |
| IM08 | Y1,κ | 2.20 × 10$^{-10}$ | <1 μg/ml |
| IMelpg2 | Y1,κ | 5.20 × 10$^{-10}$ | 1 μg/ml |
| IM06 | Y1,κ | 2.30 × 10$^{-10}$ | 2 μg/ml |
| IM09 | Y1,κ | 1.40 × 10$^{-10}$ | 16 μg/ml |
| IM13 | Y1,κ | 1.30 × 10$^{-10}$ | 2 μg/ml |
| IM19 | Y1,κ | 2.20 × 10$^{-10}$ | >16 μg/ml |
| IM20 | Y2a,κ | 0.74 × 10$^{-10}$ | 2 μg/ml |

[a]Affinity of Ab2s to MEM136 was determined as follows: Different concentrations of $^{125}$I-MEM136 were added to each well preincubated with Ab2 (100 ng/well) for 18 hours at 4° C.. A count of 10 μl and aliquot from each well was taken to determine the free $^{125}$I-MEM136. The plates were washed and the bound $^{125}$I-MEM136/well determined. Affinity was measured by the Schatchard analysis of the equilibrium binding of $^{125}$I-MEM136 to different Ab2s, and Kd values in molar quantity were determined.
[b]IC$_{50}$ is the concentration of an Ab2 required for a fifty percent inhibition of $^{125}$I-MEM136 binding to the melanoma cell line Colo38.

Figure 11:
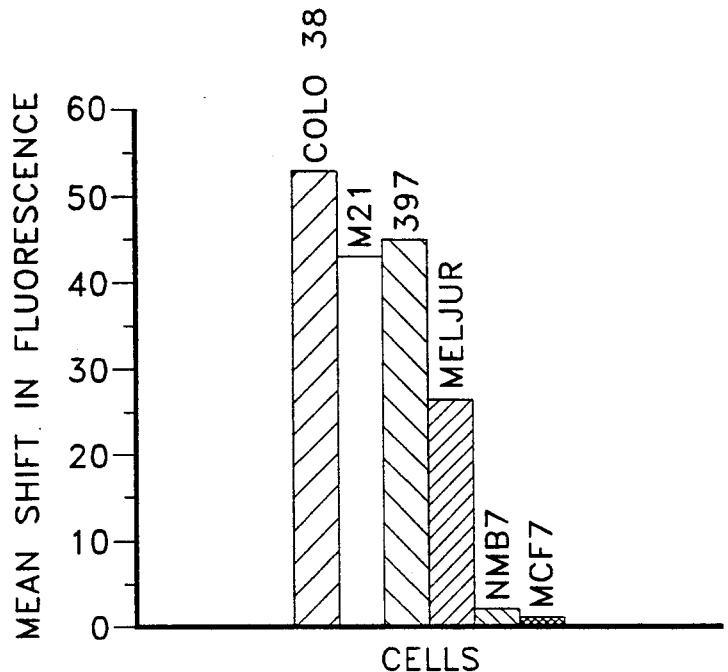
FIG. 11 depicts the Ab1' response in sera of rabbits immunized with IMelpg2 in MDP-A as determined by IIF analysis.

ELISA binding data were confirmed by IIF analysis using IMelpg2 and IM06 immune rabbit sera obtained seven days after the fourth immunization (FIG. 10). Colo38 and NMB7 cells were incubated with different dilutions of sera washed and subsequently labelled with fluorescein-conjugated goat anti-rabbit IgG. Panel (a) IMelpg2 immune sera on Colo38, (b) IMelpg2 immune sera on NMB7, (c) IM06 immune sera on Colo38, and (d) IM06 immune sera on NMB7. Sera of rabbits immunized with MOPC21 in MDP-A were employed as control, panel (e). The data presented in the figure were obtained with serum dilutions of 1:500. Sera from rabbits immunized with either IM06 or IMelpg2 bound only to MPG-+ Colo38 cells and not to MPG- NMB7 cells. Use of the MDP-A adjuvant was required for the effective induction of Ab3 responses, in agreement with previous observations (Chattopadhyay, et al., J. Immunol., submitted (1990)). To demonstrate that the anti-anti-id immune sera only react to NTG+ cells, the IMelpg2 immune sera was further tested against various MPG+ and MPG− cells. Different MPG+ cells, Colo38, M21, 397, Meljur and MPG− cells, NMB7 and MCF-7 were incubated with 1:500 dilution of serum washed and labeled with fluorescein-conjugated goat anti-rabbit IgG. Results shown in FIG. 11 demonstrate that the reactivity of IMelpg2 immune sera co-type with MTG expressing cell lines.

Figure 12:
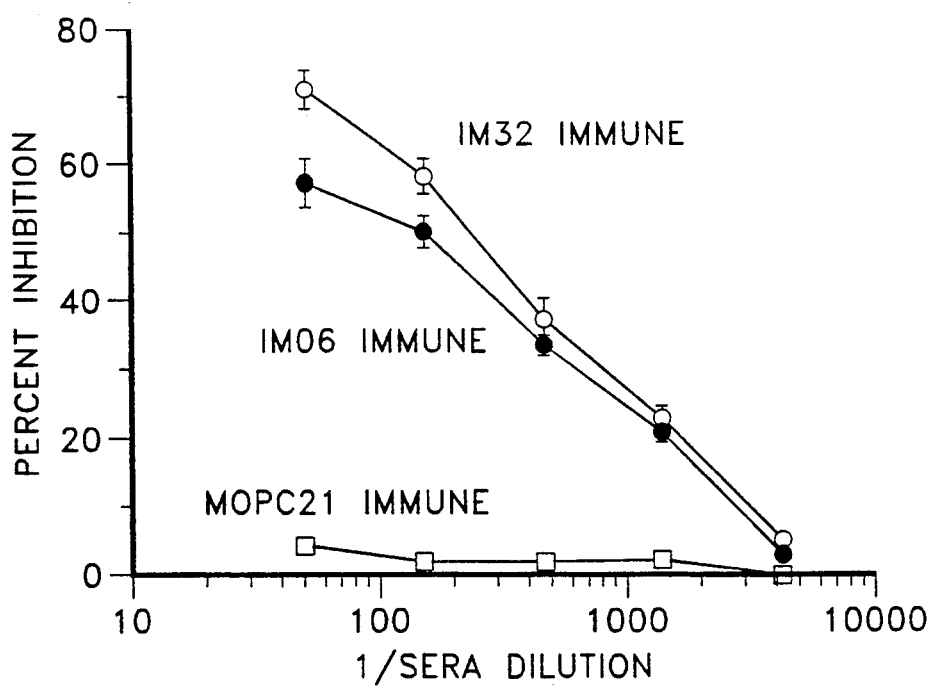
FIG. 12 shows the total idiotype (Ab3) response in sera of rabbits immunized with IMelpg2 or IM06 with MDP-A.
Figure 13:
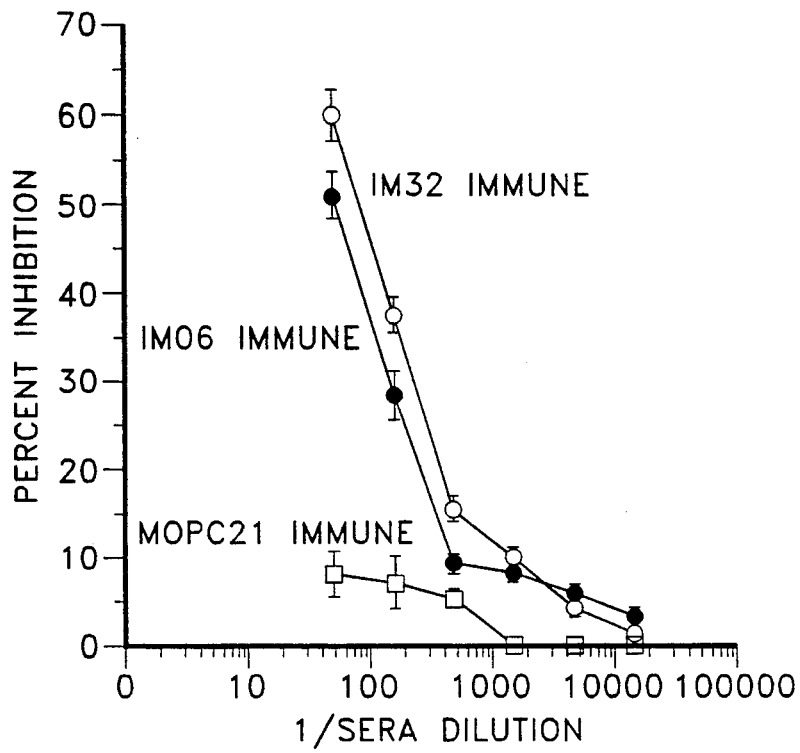
FIG. 13 depicts the Ab1' response in sera of rabbits immunized with IMelpg2 or IM06 in MDP-A.

Total Ab3 response was analyzed by a homologous inhibition assay where binding of $^{125}$I-MEM136 to F(ab')$_2$ fragments of IMelpg2 or IM06 was studied at different dilutions of IMelpg2 or IM06 immune sera. Sera from rabbits immunized with MOPC21 in MDP-A were used as control. The results are expressed as percentages of inhibition which are arithmetic means of triplicate determinations. As shown in FIG. 12, both IMelpg2 and IM06 induced Ab3 responses in rabbits of similar magnitude. A 50% inhibition of $^{125}$I-MEM136 binding to IMelpg2 was achieved at a 1/250 dilution of sera from rabbits immunized with IMelpg2. On the other hand, a 1/150 dilution of sera from rabbits immunized with IM06, was required to produce a similar level of inhibition. Next, it was demonstrated that both IMelpg2 and IM06 immune sera inhibited the binding of $^{125}$I-MEM136 to Colo38 (FIG. 13). The Ab1' response was analyzed by inhibition of binding of $^{125}$I-MEM136 to Colo38 cells using different dilutions of sera. The anti-mouse activity was eliminated by passing the rabbit sera through normal mouse IgG-sepharose 4B. The results are expressed as percentages of inhibition which are arithmetic means of triplicate determinations. Sera from rabbits immunized with MOPC21 in MDP-A were used as control. A 50% inhibition of binding of MEM136 to Colo38 was achieved at approximately a serum dilution of 1:100. These results demonstrate that monoclonal anti-id can be used to induce tumor specific anti-tumor responses in rabbits that are idiotypically crossreactive with the Ab1 and also that the Ab1 and Ab1' are recognizing the same epitope on the MPG antigen. Therefore, no significant difference in total Ab3 and Ab1' responses could be seen in rabbit sera immunized with IMelpg2 and IM06.

Induction of Ab3 Response in Mice

Figure 14:
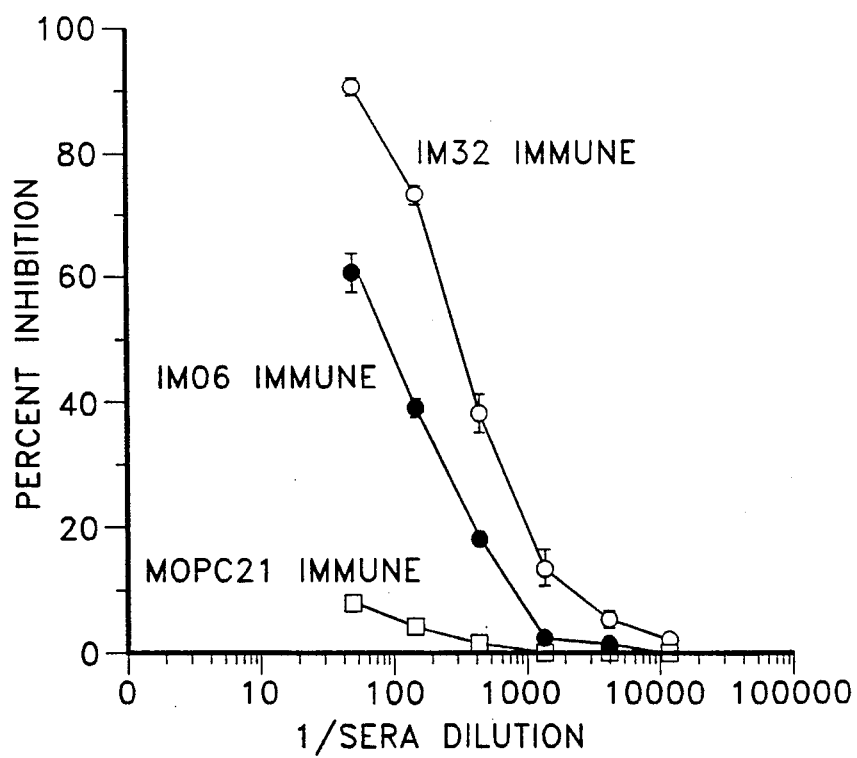
FIG. 14 depicts the total idiotype (Ab3) response in sera of mice immunized with IMelpg2 or IM06 with MDP-A.
Figure 16:
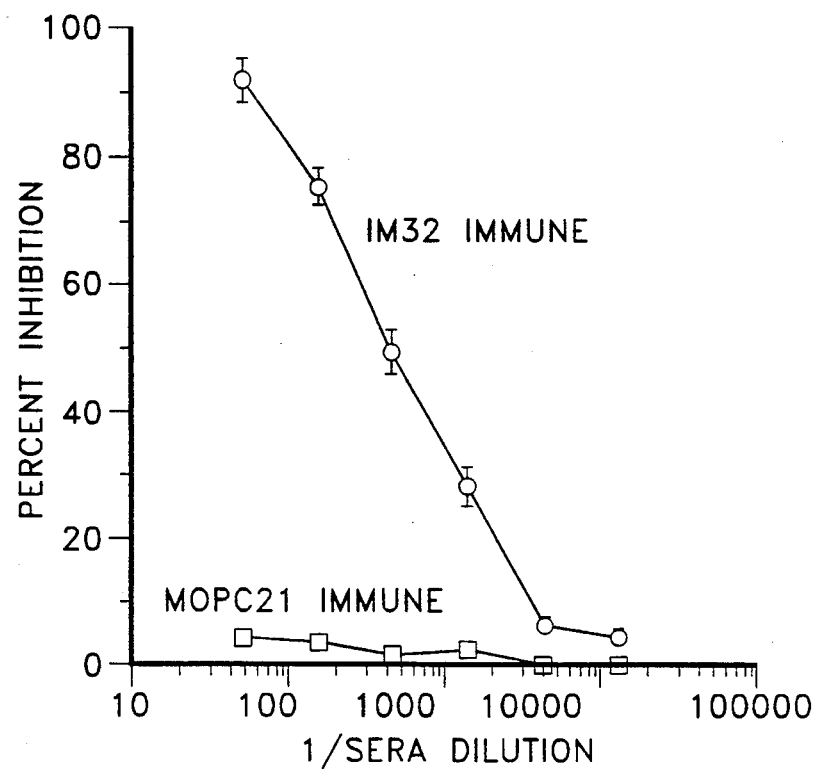
FIG. 16 depicts the Ab1' response in sera of mice immunized with IMelpg2 with MDP-A as assayed by inhibition of MEM136 binding to Colo38.

Having established that both IMelpg2 and IM06 are capable of inducing anti-MPG response, in an xenogeneic situation, I investigated whether these Ab2s induced similar responses in an allogeneic system. BALB/c mice were immunized with the A/J-derived IMelpg2 and IM06 in MDP-A. Mice were bled and tested for Ab3 and Ab1' response. The results are shown in FIGS. 14, 15 and 16. The data in FIG. 14 demonstrate that IMelpg2 and IM06 induced Ab3 responses in BALB/C mice. The results are expressed as percentages of inhibition which are arithmetic means of triplicate determinations. Sera of mice immunized with MOPC21 in MDP-A were employed as control. A 1:300 dilution of sera from mice immunized with IMelpg2 in MDP-A inhibited 50% of binding of mAb MEM136 to IMelpg2 and a 1:90 dilution of sera from mice immunized with IM06 was required to produce the same inhibition of binding. However, as shown in FIG. 15, IIF analysis demonstrated that, in mice, only IMelpg2 induced an antibody response reactive with the melanoma cell line, Colo38. Colo38 and NMB7 cells were incubated with different dilutions of sera and labeled with fluorescein-conjugated goat anti-mouse IgG. Panel (a) shows the binding of IMelpg2 immune sera on Colo38, (b) represents binding of IMelpg2 immune sera on NMB7; panels (c) and (d) demonstrate the binding of IM06 immune sera to Colo38 cells and NMB7 cells, respectively. Sera of mice immunized with MOPC21 in MDP-A were employed as control (e). The data presented in the figure were obtained with a serum dilution of 1:50. Reliable binding of IMelpg2 Ab1' antisera to Colo38 cells could be detected in 6/6 mice tested, even at a serum dilution of 1:1000. In contrast, mice immunized with IM06 in MDP-A did not develop antibodies reacting with melanoma cells even at a dilution of 1:50. The binding of the Ab1', induced by IMelpg2, was specific, as demonstrated by the inability of immune sera to bind to MPG- NMB7 cells and also by the inability of control MOPC21 immune sera to bind to Colo38 cells.

To compare the epitope specificity of Ab1 and the induced Ab1', I tested whether IMelpg2 immune sera can inhibit the binding of $^{125}$I-MEM136 to Colo38 cells. The results are shown in FIG. 16. The Ab1' response was analyzed by inhibition of binding of $^{125}$I-MEM 136 to Colo38 cells by different dilutions of sera. The results are expressed as percentages of inhibition which are arithmetic means of triplicate determinations. Sera from mice immunized with MOPC21 were used as control. A 50% inhibition of binding MEM136 to Colo38 was achieved at a 1/400 dilution of sera. These results indicate that a monoclonal anti-id can be used to induce anti-tumor responses in allogenic mice which are idiotypically crossreactive with the Ab1. These results also suggest that Ab1 and Ab1' are recognizing the same epitope on the MPG antigen.

Affinity Purified Rabbit Ab3 Contains Anti-MPG Reactivity

Figure 19:
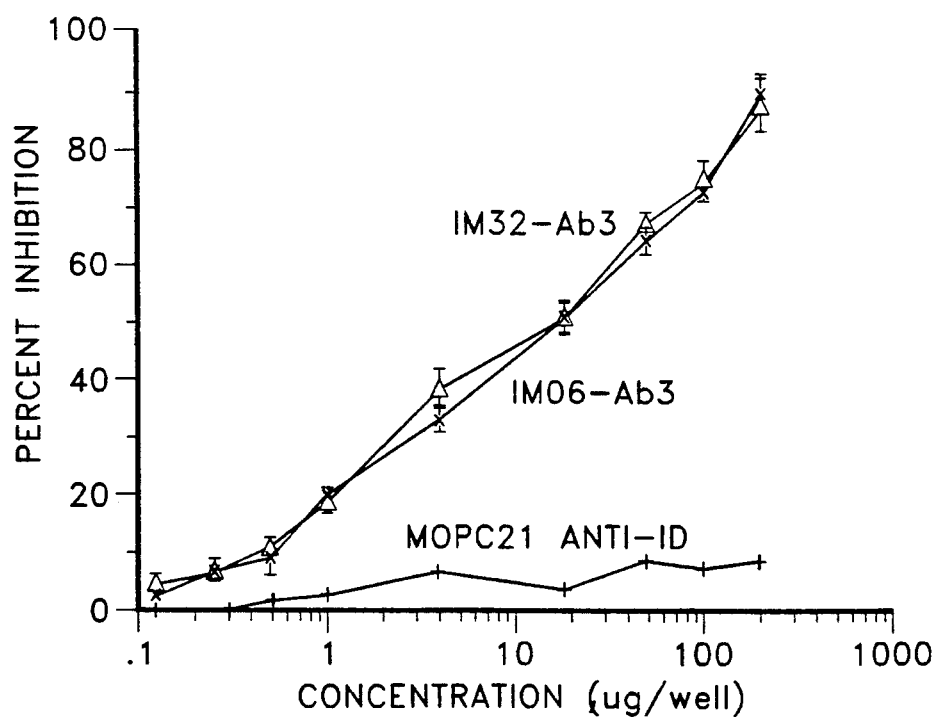
FIG. 19 shows the inhibition of binding of $^{125}$I-MEM136 to Colo38 cells by affinity purified rabbit Ab3s obtained from rabbits immunized with IMelpg2 or IM06 in MDP-A.
Figure 18A:
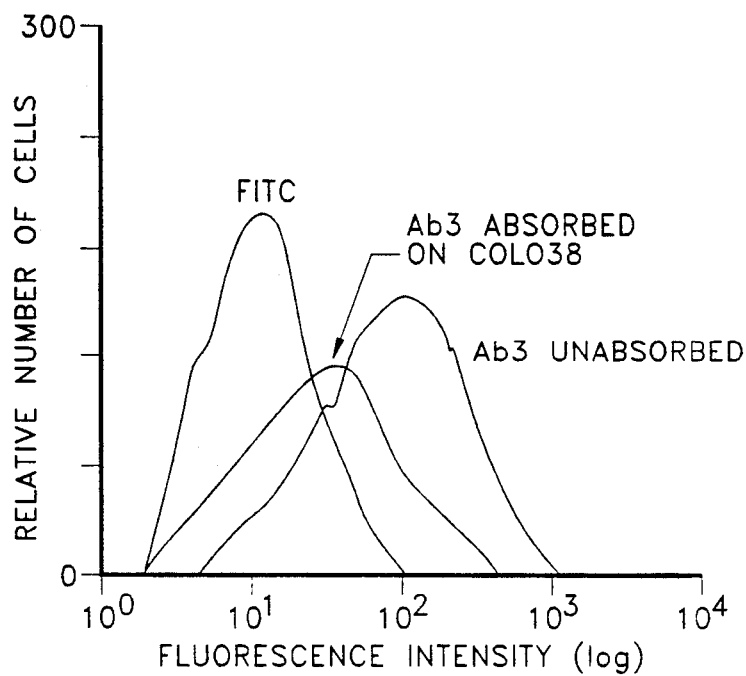
FIGS. 18A & 18B depict the IIF analysis of IMelpg2-Ab3 on Colo38 (MPG+) cells before and after absorption on Colo38 and NMB7 cells.
Figure 18B:
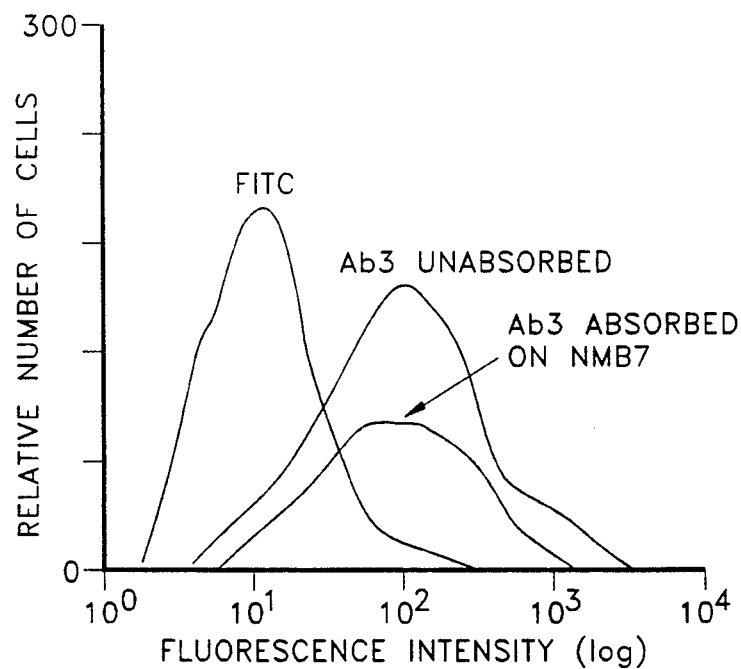

To demonstrate that the anti-anti-idiotype antibodies (Ab3s) are the active component in the IMelpg2 and IM06 immune sera, Ab3s were purified from immune sera. Colo38 and NMB7 cells were incubated with 10 μg of Ab3 purified from rabbits immunized with IMelpg2 or IM06 in MDP-A. The results are shown in FIG. 17, Panels (a) and (b) show profiles obtained by incubating IMelpg2-Ab3 with Colo38 or NMB7 cells while panels (c) and (d) shows the profiles obtained with IM06-Ab3 incubated with Colo38 or NMB7 cells. Panel (e) shows the profile obtained with 10 μg of MOPC21. The data presented in FIG. 17 suggest that purified Ab3s from IMelpg2 and IM06 immune sera bind to Colo38 (MPG4-) and not to NMB7 (MPG-) cells. As expected, these purified Ab3s were found to be idiotypically cross-reactive with the Ab1 as determined by the ability of these Ab3s to inhibit binding of $^{125}$I-MEM136 to IMelpg2 or IM06. The specificity of these Ab3s was further supported by absorption of Ab3s on Colo38 and NMB7 cells. FIG. 18 shows that the Ab1' response is depleted when IMelpg2-Ab3 was absorbed with Colo38 cells but not with NMB7 cells. Similar results were observed with IM06-Ab3. Finally, as shown in FIG. 19, the cross-reactivity of epitope specificity of IMelpg2-Ab3, IM06-Ab3 and the Ab1 was demonstrated by the ability of purified Ab3 to inhibit the binding of MEM136 to Colo38. The percentages of inhibition were computed and the average obtained with two rabbits is shown. MOPC21 anti-id antibodies were used as control.

Fine specificity of mice and rabbits Ab3s

Figure 20A:
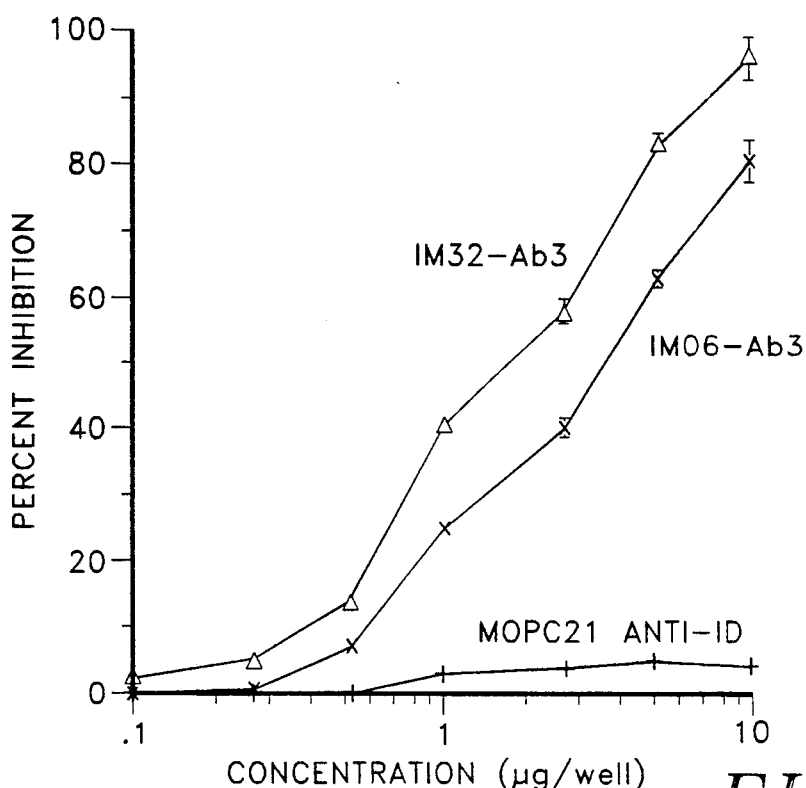
FIGS. 20A and B shows the inhibition of binding of $^{125}$I-IMelpg2-Ab3 to IMelpg2 by various concentrations of unlabeled IMelpg2-Ab3 and IM06-Ab3, (A) and the inhibition of $^{125}$I-IMelpg2-Ab3 binding to IMelpg2 by different dilutions of sera from mice immunized with IMelpg2 or IM06 (B).
Figure 20B:
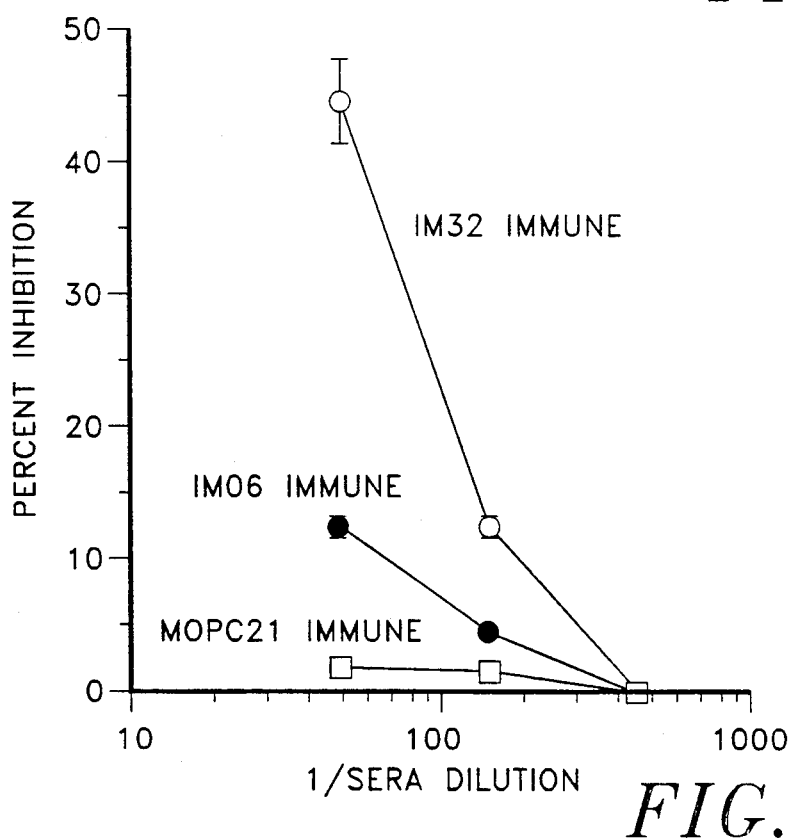

For the qualitative analysis of the Ab3s induced by IMelpg2 and IM06 in mice and rabbits, I analyzed $^{125}$I-IMelpg2-Ab3 binding to IMelpg2 in the presence of different concentrations of purified IMelpg2-Ab3, IM06-Ab3 and MOPC21 anti-id antibody. Both the murine IMelpg2- and IM06- immune sera were also used in the same inhibition analysis. A typical inhibition curve is shown in FIG. 20 demonstrating that IMelpg2 induces idiotypically similar Ab3s in mice and rabbits. In (a), MOPC21-anti-id was used as a control; in (b), MOPC21-immune mouse sera was used as a control. Furthermore, in rabbits, IMelpg2 induces Ab3s which are very similar to those induced by IM06. However in mice, IM06-induced Ab3s did not compete well with $^{125}$I-IMelpg2-Ab3 binding to IMelpg2, confirming the notion that, in mice, IMelpg2 and IM06 are behaving immunologically differently.

Figure 21A:
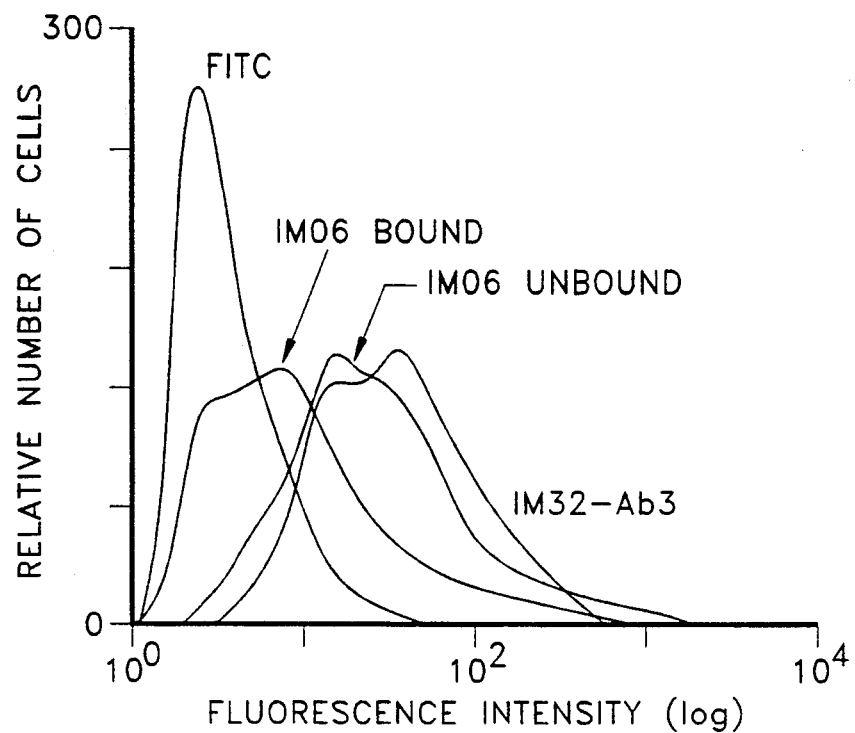
FIGS. 21A and 21B depict the Ab1' response profile in the IMelpg2-Ab3 population absorbed on IM06.
Figure 21B:
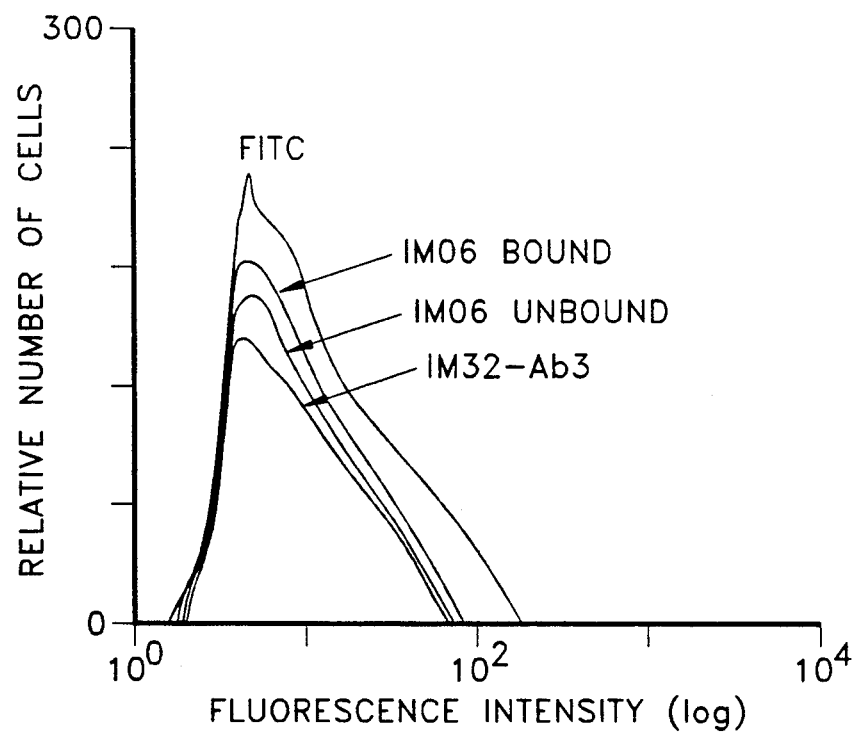
Figure 22:
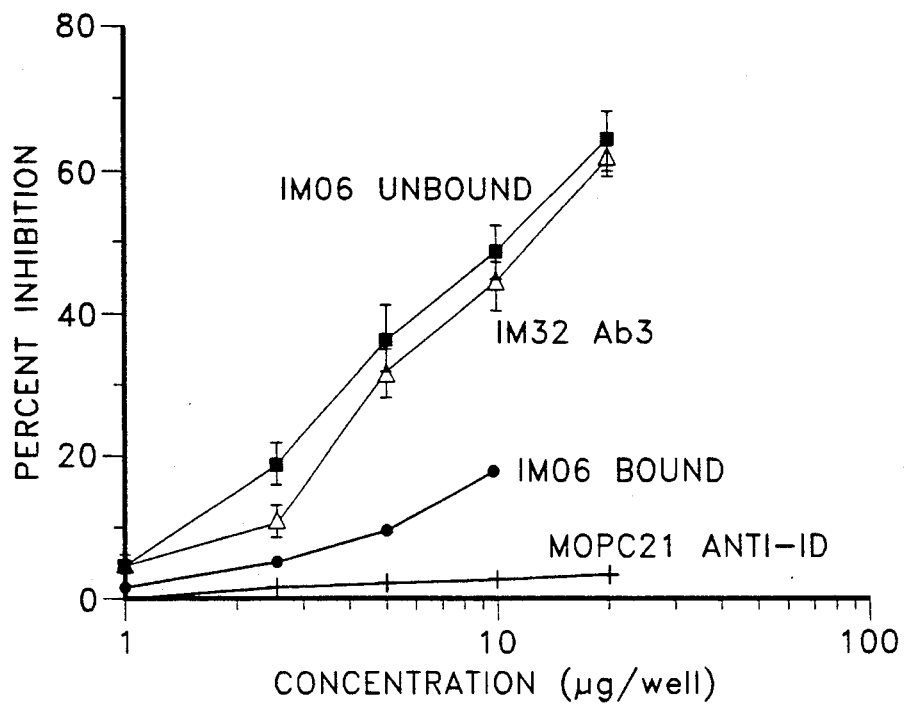
FIG. 22 shows the idiotype response of IMelpg2-Ab3, before and after absorption on IM06-sepharose using inhibition of binding of $^{125}$I-MEM136 to IMelpg2.
Figure 23:
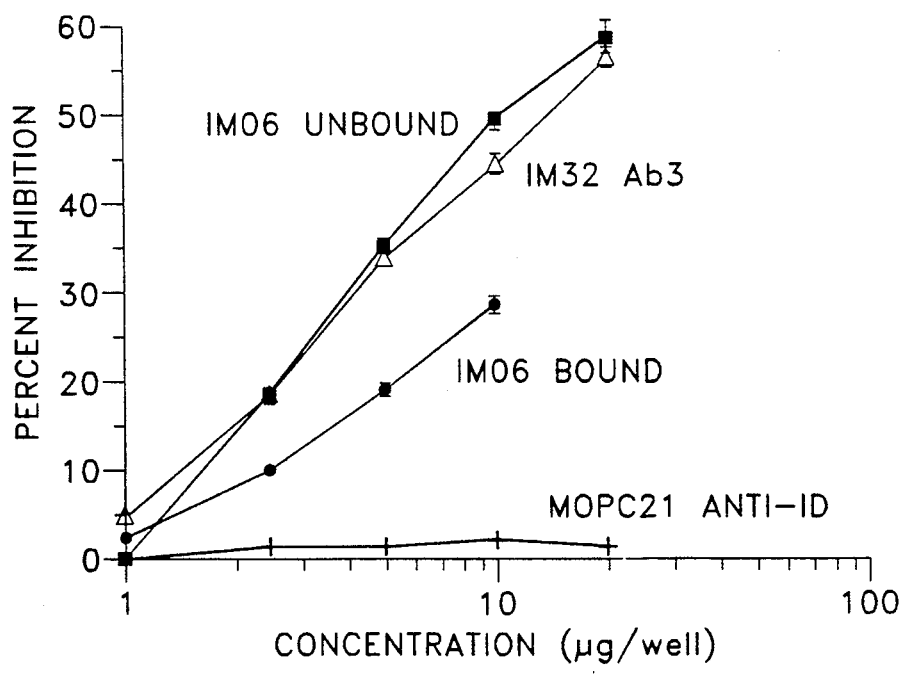
FIG. 23 shows the inhibition of binding of $^{125}$I-MEM136 to Colo38 by IMelpg2-Ab3, before and after absorption on IM06-sepharose column.

To further dissect idiotypic crossreactivity between IMelpg2-Ab3 and IM06-Ab3 population in rabbits, IMelpg2-Ab3s were absorbed on IM06-Sepharose column. It should be stated that 10-20% of the IMelpg2-Ab3 population was crossreactive with IM06 idiotype because that was the amount bound to IM06 column. The fractions bound and unbound on IM06 idiotypes were examined for tumor cells binding and for their ability to inhibit the binding of MEM136 to IMelpg2 or melanoma cell line, Colo38. As shown in FIG. 21, IIF analysis was performed using IMelpg2-Ab3, before and after absorption on IM06-sepharose against (a) Colo38 (MPG+) cells and (b) NMB7 (MPG-) cells. The fluorescein-conjugated goat anti-rabbit IgG was used for staining. These results demonstrate that the majority of Ab1' fraction in the IMelpg2-Ab3 population remains in IM06 unbound fraction. That is, the majority of the Ab1' fraction in IMelpg2-Ab3 population is idiotypically noncrossreactive with IM06. FIGS. 22 and 23 confirm the tumor cell binding study that indeed the whole IMelpg2-Ab3 population and the population depleted of IM06 idiotype contain crossreactive populations with the Ab1, MEM136. However, from FIGS. 22 and 23, it is also apparent that IMelpg2-Ab3 population bearing IM06 idiotype is to a lesser extent cross-reactive with MEM136.

Discussion

Applicant analyzed the ability of eight Ab2s to induce anti-MPG responses in mice and rabbits crossreacting with human melanoma cells. All eight Ab2s are idiotypically crossreactive and are specific for their common Ab1, MEM136 combining site[3]. I initially immunized rabbits with all eight Ab2s for the induction of anti-MPG responses. Out of eight Ab2s tested, only IMelpg2 and IM06 induced anti-MPG responses in rabbits. On the other hand, both IMelpg2 and IM06 induced equivalent amount of Ab3 responses in allogeneic mice. However, in allogeneic mice only IMelpg2 induced anti-MPG responses.

Earlier studies characterized various types of Ab2s obtained after immunization with an Ab1 (Jeme, et al., EMBO J., 1:243 (1982); Bona, et al., *Monoclonal and Anti-idiotypic Antibodies: Probes for Receptor Structure and Function*, p. 141 (1984)). The internal image or Ab2β class of antibodies is believed to mimic serologically an epitope on the antigen used to generate the original Ab1 and can be used to generate an antigen specific response in place of nominal antigen. This class of Ab2s is also capable of inducing an antigen specific response across the species barrier. Alternatively, the non-internal image class of Ab2s (Ab2α) may or may not be directed against a combining site related idiotope and will not induce an antigen specific response across the species barrier. Based upon their serologic characteristics, IMelpg2 may belong to the internal image class of antibodies while IM06 may belong to the non-internal image class of antibodies. The Ab3 response induced by IMelpg2 is idiotypically crossreactive with it's Ab1 (Ab3s inhibited the binding of MEM136 to IMelpg2). Further, the anti-MPG response induced by IMelpg2 in mice and rabbits reacted to MPG+ melanoma cells and also inhibited the binding of Ab1 to Colo38. Therefore, the Ab1 and the Ab1' response induced by IMelpg2 share similar antigenic specificity.

The Ab3 response induced by IM06 in mice and rabbits is idiotypically crossreactive with MEM136, as demonstrated by the ability of Ab3s, from both mice and rabbits, to compete with MEM136 to bind to IMelpg2 or IM06. However, IM06-immune mouse sera neither bound to Colo38 cells nor competed with MEM136 to bind to Colo38 cells. To further characterize the serologic mimicry between the MPG epitope and the Ab2s, anti-Colo38 sera from mice and rabbits were tested in a direct binding RIA to determine whether they bound to IM06 or IMelpg2 and also were tested to determine whether they could compete with MEM136 to bind to Colo38, IMelpg2 or IM06. No detectable binding to Ab2s or inhibition of MEM136 to Ab2s by the sera could be observed. Therefore, although Colo38 cells contain a high density of MPG molecules on their surface, there is no evidence for an anti-MPG response in Colo38 immunized rabbit sera which is idiotypically crossreactive with MEM136. Although immune sera from animals immunized with purified MPG antigen were not examined, Ab2s are apparently activating silent clones as has been demonstrated by others (Bona, et al., *J. Exp. Med.*, 153:951 (1981); Hiernaux, et al., *J. Exp. Med.*, 153:1004 (1981)). The inability of IM06 to induce an anti-MPG response in mice could be due to the fact that mice lack the IM06 idiotype. Alternatively, IM06 may be inducing a regulatory mechanism which interferes with its ability to induce id+Ag+ responses.

Recently, Shearer et. al., *J. Immunol.*, 145:932 (1990) generated four monoclonal Ab2s against a monoclonal anti-SV-40-T antigen that are idiotypically crossreactive. They examined only one Ab2 for the induction of anti-SV-40 antibody response. They argued that, as all Ab2s are crossreactive, one Ab2 should represent all. My data indicate that Ab2s against an Ab1 can be highly crossreactive, yet differ drastically in their ability to induce antigen specific responses in different species. Therefore, to identify a potential idiotype-based active immunotherapeutic agent, one ought to immunize various Ab2s in various species as described earlier (Nisonoff, et al., *Clin. Immunol. Immunopathol.*, 21:397 (1981)).

The induction of Ab3 responses in rabbits by IMelpg2 and IM06 warrants some discussion. The Ab3s induced by these two Ab2s are idiotypically crossreactive (i.e. the Ab3s inhibited the binding of IMelpg2-Ab3 to IMelpg2). Applicant's data also indicate that both Ab3s are recognizing an epitope defined by the Ab1 (i.e., the Ab3s inhibited the binding of MEM136 to melanoma cells). However when the IMelpg2-induced Ab3 was separated on an IM06 column, two fractions were obtained. Eighty to ninety percent of the Ab3 population did not bind to IM06 column (IM06 id−) and contained the majority of the IMelpg2-Ab3 idiotype and Ab1' reactivity. Ten to twenty percent of the IMelpg2-Ab3 population bound to IM06 (IM06 id+) inhibited poorly the binding of MEM136 to IMelpg2 or melanoma cells (i.e., contain little to no Ab1'). Similar results were observed with IM06 immune rabbit sera indicating that the majority of the IM06-Ab3s in rabbits are IM06 id specific and contained Ab1' reactivity. Therefore, two Ab2s made against the same Ab1 induced a different population of Ab3 response. The IMelpg2-specific idiotype (IMelpg2 id+IM06 id−) may contain an antigen image or regulatory components necessary for the induction of anti-TAA response across the species barrier. The weak inhibition of MEM136 binding to IMelpg2 or Colo38 cells by the (IM06 id+ IMelpg2 id+)population could be due to the low affinity of crossreactive Ab3 population for IMelpg2 and for the MPG antigen on Colo38 cells.

In summary, I have analyzed the Ab3 response in rabbits by eight highly crossreactive Ab2s generated against an MoAb1. Only two, IM06 and IMelpg2, induced specific anti-MPG responses. When tested in mice, only IMelpg2 induced specific anti-MPG responses. The majority of the Ab3 and Ab1' reactivity in the IMelpg2-Ab3 population in rabbits could be attributed to the IMelpg2 id+ IM06 id− population. The epitope specificity of Ab1' induced by IMelpg2 in mice and rabbits is similar to the original Ab1, MEM136. The Ab2, IMelpg2, is a potentially important active immunotherapeutic agent in melanoma patients. Collectively, the data indicates that IMelpg2 (hybridoma cell line producing the IMelpg2 antibody deposited with the ATCC 12301 Parklawn Dr., Rockville, Md. 2085, Oct. 18, 1989, ATCC designation No. HB 10265) is the most promising candidate for inducing an anti-tumor response in active immunotherapy. EXAMPLE 4

Immunological Equivalents of IMelpg2

This invention is not limited to IMelpg2. Indeed, many anti-idiotypic antibodies can be made that are directed to the idiotype of the murine monoclonal antibody MEM136. Any monoclonal antibody secreted by hybridomas from any species, as well as any polyclonal (i.e., conventional antisera from any species), with the same immunological specificity or specificity may be used. It also will be appreciated by those skilled in the art that derivatives of the murine monoclonal MEM136 may also be used. As used herein, the term "derivative" includes (but is not limited to) related cell lines as well as any antibody or antibody fragments including synthetic peptides that may compete, completely or partially with monoclonal antibody MEM136 for binding to MPG.

To practice this invention with anti-idiotype antibodies equivalent to IMelpg2, the first step is to identify idiotypic components reactive with the specific determinant (epitope) of a MPG antigen. This may be accomplished by any of several approaches known to those skilled in the art. For example, similar antibodies (Ab1s) with specificity for the MPG antigen epitope recognized by MEM136 may be obtained from melanoma patients, experimental animals immunized with human melanoma cells, from commercial sources, or by methods routinely practiced by those skilled in the art. For purposes of this invention, the Ab1 may be either polyclonal or monoclonal antibodies. Polyclonal antibodies can be isolated from patients' or animals' sera by affinity purification using immobilized disease associated antigens as described by Real, et al., *J. Exp. Med.*, 160:1219 (1984) and in the *Handbook of Experimental Immunology* (ed. Weir, et al., (1986)) (hereinafter referred to as "the Handbook"). Monoclonal antibodies can be generated by standard somatic cell hybridization rescue fusion ("rescue fusion") using standard techniques practiced in the prior art (see the Handbook, supra and Carol, et al., *J. Immunol. Meth.*, 89:61 (1986)) and utilizing patients' peripheral B cells, or any other B-cells sensitized to a MPG antigen. Polyclonal and monoclonal antibodies can also be generated using the techniques described above from human subjects or experimental animals inoculated with tumor, with tumor extracts, purified MPG or peptides derived from MPG.

These MEM136 equivalent Ab1 antibodies (i.e., those that compete with IMelpg2 for binding to the MPG) could be utilized to generate and identify anti-id Ab2s with immunological specificity identical or similar to IMelpg2.

EXAMPLE 5

Use of the Anti-idiotype Antibodies in Diagnosis, Monitoring and Immunotherapy The anti-idiotypic antibodies of this invention may be used in disease diagnosis and monitoring, and in active or passive immunotherapy according to the following methods. (Although the following discussion will describe the use of IMelpg2 in disease diagnosis and monitoring and in active or passive immunotherapy, those skilled in the art will recognize that the methods apply, as well, to IMelpg2 equivalents).

In disease diagnosis and monitoring IMelpg2 may be incorporated into in vitro assays (such as ELISA or RIA) in order to measure the levels of serum idiotypes reactive with IMelpg2 before, during and after immunotherapy; for example, in measuring the booster effect of multiple administrations of IMelpg2 in active immunotherapy.

In active immunotherapy, IMelpg2 may be administered in order to heighten the immune response to stimulate beneficial components of the immune system; for example, in treatment of malignant melanoma, it is desirable to elicit humoral and cellular responses directed against the melanoma associated antigen. More specifically with respect to melanoma, it is known that tumor cells traverse extra cellular matrix ("ECM") during the process of invasion and metastasis. The ECM that is most relevant to metastasis is the basal lamina or basement membrane. Basement membranes are composed mainly of collagen type IV meshed laminin, entactin, fibronectin and proteoglycans. A majority of experimental evidence suggests a close correlation between extracellular membrane degradation and tumor cell invasion and metastasis. Therefore, Ab3 attachment to ECM may interfere with the biology of tumor growth and metastasis by inhibiting the binding of tumor cells to ECM. Taken together, Applicant's data demonstrate the utility of IMelpg2 as an active melanoma immunotherapeutic agent. IMelpg2 also may be useful inducing protective immunity.

When used in active immunotherapy, the anti-idiotype antibodies of the present invention are preferably administered in an adjuvant formulation meaning adjuvants, carriers, vehicles and conjugation techniques known or developed by those skilled in the art. Such formulations may incorporate Syntex Adjuvant Formulation-1 (SAF-1), muramyl dipeptide derivatives, lipopolysaccharides, pluronic polymers, Bacillus Calmette-Guérin ("BCG"), liposomes, mineral oil emulsions, alum adjuvants, such as aluminum hydroxide and aluminum phosphate, saponins such as Quil A, immunestimulating complexes ("ISCOMS"), lipid A, keyhole limpet hemocyanin (KLH), hepatitis core antigen, tetanus toxoid, water-in-oil emulsions, glutaraldehyde crosslinking and other conjugation procedures to conjugate the anti-idiotype antibodies to adjuvants or carriers. Examples of adjuvant formulations incorporating these materials and processes have been described in Steinberger, et al., *Experimental Parasitology*, 58:223–229 (1984); Morein, *Nature* 332: 287–288 (1988); Allison, *J. Immunol. Methods*, 95:157–168 (1986); Clarke, et al., *Nature* 330:381–384 (1987); Raychaudhuri, et al., *J. Immunol.* 137:1743 (1986); Eskola, et al., *New Eng. J. Med.* 317:717–722 (1987); Allison, *Bio/Technology* 5:1041 (1987); Leonard, et al., *Blood* 65:1149–1157 (1985); *Practical Guide for Use in Affinity Chromatography and Related Techniques* (2nd ed. 1983 by Reactiff IBF) pub. Societe Chemique Pointet-Girard, France.

When used in active immunotherapy, the antibodies are administered to the patient in a manner and dose that will induce tumor regression. They generally will be administered by subcutaneous or intramuscular (IM) injection. The proper dosage of Ab2 to be administered to a particular patient will depend on the patient's size and the status of their immune system function. Dosages may range from 500 μg to 5 mg. The preferred dosage range to be administered would be 100 μg to 5 mg per injection site. Of course, the objective is to use the minimum dose shown to provide efficacious humoral and/or cellular anti-tumor responses. Multiple injection sites may be used.

With regard to the use of the antibodies of this invention in passive immunotherapy, there may be instances of disease (for example, autoimmune disease) in which MPG is a target of deleterious B-cell or T-cell immune responses that are attacking healthy tissue. Passive immunotherapy may be used in this circumstance of disease. When used in passive immunotherapy, the antibodies herein disclosed are not used in adjuvant formulations. The method of administration is intravenous injection and generally, larger doses of antibody are given (in the range of 50 mg to 5 g). Other uses of these antibodies in passive immunotherapy will be apparent to those skilled in the art. Generally, passive immunotherapeutic uses of these antibodies will be appropriate whenever the MPG is the target of immune responses that one wishes to suppress.

Hybridoma cell line producing the IMelpg2 antibody, as noted in Example 3, was deposited with the American Type Culture Collection on Oct. 18, 1989, under the provisions of the Budapest Treaty on the International Recognition of the Deposit of Microorganisms for the Purpose of Patent Procedures ("Budapest Treaty"). The producing cell line which was deposited was determined to be viable on Oct. 25, 1989. The IMelpg2 producing cell line has been assigned the following accession number by the ATCC: HB10265. In accordance with the provisions of the Budapest Treaty, the inventor agrees that all restrictions upon public access to this deposit will be irrevocably removed upon the grant of a patent by the United States Patent and Trademark Office. The inventor further agrees that the deposit will be replaced if viable samples cannot be dispensed by the ATCC.

I claim:

1. Hybridoma cell line having ATCC accession No. HB10265.

2. A monoclonal antibody produced by the cell line of claim 1.

* * * * *